United States Patent [19]

Venuti

[11] Patent Number: 4,739,056

[45] Date of Patent: Apr. 19, 1988

[54] N-N-DISUBSTITUTED-OMEGA-(2-AMINO-3-(CARBONYLMETHYL)-3,4-DIHYDROQUINAZOLINYL)OXY-ALKYLAMIDES AND RELATED COMPOUNDS

[75] Inventor: Michael C. Venuti, San Francisco, Calif.

[73] Assignee: Syntex (U.S.A.) Inc., Palo Alto, Calif.

[21] Appl. No.: 935,659

[22] Filed: Nov. 26, 1986

[51] Int. Cl.[4] ............... C07D 239/84; A61K 31/495
[52] U.S. Cl. .................................. 544/292; 544/119
[58] Field of Search ........................... 544/292, 119

[56] References Cited

U.S. PATENT DOCUMENTS

| | | | |
|---|---|---|---|
| 3,535,321 | 10/1970 | Dunn | 544/292 |
| 4,146,718 | 3/1979 | Jenks et al. | 514/292 |
| 4,490,371 | 12/1984 | Jones et al. | 544/250 |
| 4,551,459 | 11/1985 | Jones et al. | 514/267 |

Primary Examiner—Glennon H. Hollrah
Assistant Examiner—James H. Turnipseed
Attorney, Agent, or Firm—Liza K. Toth; Tom M. Moran

[57] ABSTRACT

Compounds are disclosed according to the formula

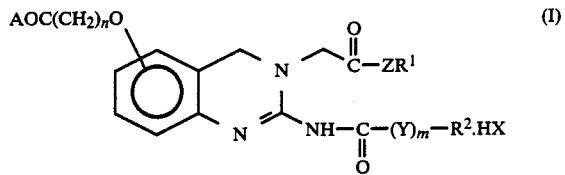

or an optical isomer thereof.

The compounds of Formula I are cyclic AMP phosphodiesterase inhibitors useful as antithrombotic and inotropic agents and the like in mammals.

18 Claims, No Drawings

N-N-DISUBSTITUTED-OMEGA-(2-AMINO-3-(CARBONYLMETHYL)-3,4-DIHYDROQUINAZOLINYL)OXY-ALKYLAMIDES AND RELATED COMPOUNDS

BACKGROUND OF THE INVENTION

1. Field of the Invention

This invention relates to novel substituted N-N-disubstituted-ω-[2-carbonylamino-3-(carbonylmethyl)-3,4-dihydroquinazolinyl]oxyalkylamides and related compounds. More specifically the compounds of interest are acylated guanidino acid, ester and amide carbonyl compounds of the above class and their pharmaceutically acceptable acid addition salts.

2. Related Art

U.S. Pat. Nos. 4,551,459 and its parent 4,490,371 issued on Nov. 5, 1985 and Dec. 25, 1984, respectively, are directed to phosphodiesterase inhibitors having inotropic and anti-metastatic activities. More specifically, these patents along with U.S. patent application Ser. No. 744,100, filed May 11, 1985, now U.S. Pat. No. 4,663,320 are directed to (2-oxo-1,2,3,5-tetrahydroimidazo[2,1-b]quinazolinyl)oxyalkylamides and their pharmaceutically acceptable acid addition salts. Additionally, U.S. patent application Ser. No. 889,641 relates to N-N-disubstituted-ω-[2-amino-3-(carbonylmethyl)-3,4-dihydroquinazolinyl]oxyalkylamides and related compounds. These disclosures are hereby fully incorporated herein by reference.

SUMMARY OF THE INVENTION

In a first aspect, this invention comprises a compound of the formula

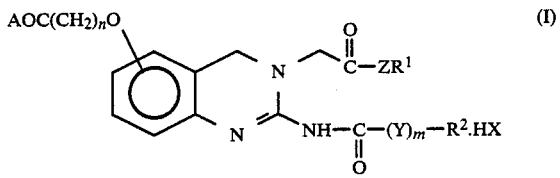

or an optical isomer thereof wherein

Y is O or $NR^4$;
Z is O or $NR^3$;
m is 0 or 1;
n is an integer of 1 to 6;
$R^1$, $R^2$, $R^3$ and $R^4$ are independently hydrogen, except that when m is 1 and Y is O, $R^2$ is not hydrogen; alkyl of 1 to 12 carbon atoms optionally substituted with a trichloromethyl or trifluoromethyl radical; cycloalkyl of 3 to 12 carbon atoms optionally substituted with up to two lower alkyl radicals; cycloalkyl lower alkyl of 4 to 12 carbon atoms optionally substituted on the cycloalkyl ring with up to two lower alkyl radicals; and phenyl or phenyl lower alkyl wherein the phenyl ring is optionally substituted with at least one lower alkyl, halo or lower alkoxy group or an $-N(R^5)_2$ group wherein $R^5$ is lower alkyl;

or independently when Y is $NR^4$ or when Z is $NR^3$, $R^2$ and $R^4$ can optionally form a first pair and $R^1$ and $R^3$ can optionally independently form a second pair respectively, in which the respective pair is combined with the N to which it is attached to form a radical selected from the group consisting of: morpholinyl, piperidinyl, N-loweralkylpiperazinyl, N-arylpiperazinyl, and pyrrolidinyl;

HX is optionally present and when present represents the acid portion of a pharmaceutically acceptable acid addition salt;

A is $NR^6R^7$ wherein $R^6$ and $R^7$ are independently selected from the group consisting of: hydrogen; alkyl of 1 to 6 carbon atoms; cycloalkyl of 3 to 8 carbon atoms or cycloalkyl lower alkyl of 4 to 12 carbon atoms wherein the cycloalkyl ring is optionally substituted with a lower alkyl, lower alkoxy, $-OCOR^5$, halo, $-N(R^5)_2$, $-NHCOR^5$, or $-COOR^5$ group wherein $R^5$ is lower alkyl; and phenyl or phenyl lower alkyl wherein phenyl is optionally substituted with at least one lower alkyl, halo or lower alkoxy group or an $-N(R^5)_2$, $-NHCOR^5$, or $-COOR^5$ group wherein $R^5$ is lower alkyl; or wherein $R^6$ and $R^7$ are combined with the nitrogen to which it is attached to form a radical selected from the group consisting of: morpholinyl, piperidinyl, perhexylenyl, N-loweralkylpiperazinyl, pyrrolidinyl, tetrahydroquinolinyl, tetrahydroisoquinolinyl, ($\pm$)-decahydroquinolinyl and indolinyl.

In a second aspect, this invention relates to a composition of matter consisting essentially of a compound of Formula I combined with at least one pharmaceutically acceptable excipient.

In a further aspect, this invention relates to a method of treating heart failure in a mammal by stimulating suppressed heart activity which occurs during heart failure.

In another aspect, this invention relates to a method of inhibiting platelet aggregation in a mammal.

In yet another aspect, this invention relates to a method for inhibiting 3',5'-cyclic AMP phosphodiesterase activity in a mammal, particularly, a human.

The above three methods comprise administering a therapeutically effective amount of a compound of Formula I alone or in admixture with a pharmaceutically acceptable excipient.

In a still further aspect, this invention relates to a compound of Formula I as defined above, except that when Z is O, $R^1$ can be, inter alia, alkyl of 3 to 12 carbon atoms rather than of 1 to 12 carbon atoms.

DETAILED DESCRIPTION OF THE PREFERRED EMBODIMENTS OF THE INVENTION

Utility

Cyclic AMP is known to regulate the activity of numerous enzymes and mediates the action of several hormones. Studies have demonstrated that a deficiency in cyclic AMP or an increase in the activity of a high affinity cyclic AMP phosphodiesterase is associated with a variety of disease states. Compounds which are inhibitors of this enzyme are useful in the treatment of hypertension, asthma, diabetes, obesity, immune dysfunctions, psoriasis, inflammation, cardiovascular disease, tumor metastasis, cancer and hyperthyroidism.

The compounds of this invention when administered to humans or mammals inhibit platelet cyclic AMP phosphodiesterase activity under physiological conditions. As a consequence, these compounds effect the inhibition of ADP-induced aggregation of human platelets. Thus, these compounds are administered to prevent or treat of a variety of conditions related to platelet aggregation and thrombosis, for example, intravascular thrombosis, prevention of coronary thrombosis, prevention of transient ischemic episodes and prevention of platelet thrombosis and the prevention of thrombosis, thrombocytopenia or platelet activation associated with the use of prosthethic devices (artificial heart valves, etc.).

Similarly, the compounds of the present invention also inhibit cardiac cyclic AMP phosphodiesterase, by cyclization under physiological conditions, resulting in a strengthening of myocardial contraction force by which the heart ventricles can pump the blood into the periphery. Consequently, these compounds also are useful as positive inotropic agents in treating myocardial failure.

Compounds of this invention exhibit certain exhibit advantages over compounds disclosed in U.S. patent application Ser. No. 889,641, and U.S. Pat. No. 4,490,371 and its continuing applications. Specifically, the instant compounds offer greater solubility and more consistent oral bioavailability than those of U.S. Pat. Nos. 4,490,371 and 4,551,459.

Definitions

The compounds of the present invention are numbered as follows:

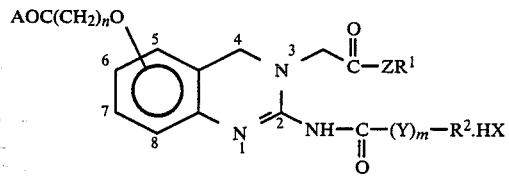

For the purposes of this disclosure, the compounds of the present invention are represented as having the single structural formula set forth as Formula I. However, all tautomers are part of this invention, and are also to be considered as represented by Formula I. Specifically, the following tautomer is part of the invention:

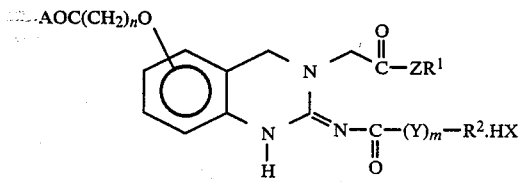

The compounds of this invention may be prepared as structural isomers wherein the oxyalkylamide side chain is substituted on the benzene ring at any of the four different available positions. This fact is graphically represented in the generic formula by the drawing of the line into the benzene ring without it being directed to a particular carbon.

Also within the scope of this invention are the optical isomers of those compounds having an asymmetric center, such as when $R^1$, $R^2$, $R^3$, $R^4$, $R^5$, $R^6$ and $R^7$ have chirality. In addition, A may be a substituent which has optical activity such as when A is a cyclic compound, or example, (+)− or (−)-decahydroquinolinyl.

Accordingly, the compounds of the present invention may be prepared either in optically active form or as racemic mixtures. Unless otherwise specified, where appropriate, products of the various synthetic steps described herein will be a racemic mixture. However, the scope of the subject invention herein is not limited to the racemic mixture, but is to encompass the separated individual optical isomers of the disclosed compounds.

If desired, the compounds herein may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers.

For the purpose of this invention, the following phrases should be understood to have the recited meaning.

When reference is made to "alkyl of 1 to 12 carbon atoms" it is meant that there is a branched or unbranched saturated hydrocarbon chain containing, in total, that number of carbon atoms. The phrase refers specifically to such substituents as, for example, methyl, ethyl, n-propyl, i-propyl, n-butyl, i-butyl, sec-butyl, tert-butyl, n-pentyl, neo-pentyl, n-hexyl and the like. The terms "alkyl of 1 to 4 carbon atoms" and "lower alkyl" are used interchangeably and mean methyl, ethyl, n-propyl, i-propyl, n-butyl, tert-butyl, i-butyl, sec-butyl, and the like. When the term "alkyl" or prefix "alk" (such as in alkoxy) is used without qualification (such as the term "lower"), a branched or unbranched saturated hydrocarbon chain having from 1 to 12 carbon atoms is contemplated.

"Lower alkoxy" means the group —OR wherein R is lower alkyl as defined in the foregoing paragraph.

An aliphatic radical is a radical having up to 16 carbon atoms, that includes carbon and hydrogen atoms, but is not aromatic, such as an alkyl, cycloalkyl, or cycloalkyl lower alkyl radical.

"Aryl" means phenyl or naphthyl, preferably phenyl.

"A cyclic secondary amine radical having from 5 to 8 atoms," as recited in the claims, means a radical derived from a commercially available secondary amine, or from a secondary amine that can be readily synthesized from a commercially available secondary amine by one of ordinary skill in the art. Examples of such radicals include morpholinyl, piperidinyl, pyrrolidinyl, and N-methyl piperazinyl.

"Carbamoyl" means the aminocarbonyl radical.

"Cycloalkyl" refers to a saturated aliphatic ring structure which contains the number of carbon atoms specified (3 to 8 carbon atoms if no specification is made), and which is substituted directly onto the Z group (i.e., oxygen or nitrogen) without any intervening methylene groups. Cycloalkyl of 3 to 12 carbon atoms includes bicyclic and tricyclic ring structures as well as unicyclic ones. Cycloalkyl radicals of 3 to 8 carbon atoms includes, for example, cyclopropyl, cyclobutyl, cyclopentyl, cyclohexyl, cycloheptyl and cyclooctyl. Cycloalkyl of 3 to 12 carbon atoms includes, for example, adamantyl as well as the foregoing radicals.

When reference is made to "cycloaklyl lower alkyl of 4 to 12 carbon atoms," it is meant that the substituents denoted as cycloalkyl of 3 to 8 carbon atoms in the preceding paragraph are attached to the nitrogen of the amide-forming group or the oxygen of the ester-forming group by means of a saturated branched or unbranched carbon chain which may have 1 to 4 carbon atoms. Such substituents are, for example, cyclohexylmethyl, cyclohexylethyl, cyclobutylmethyl, 4-cyclobutylbutyl, cyclopentylmethyl, 4-cyclopentylbutyl, cyclohexylmethyl, 4-cyclohexylbutyl, cycloheptylmethyl and 4-cycloheptylbutyl, to name a few examples.

In addition, the cycloalkyl or cycloalkyl lower alkyl radicals recited in the two foregoing paragraphs may be substituted on the ring with up to two lower alkyl radicals.

Glycine-N-cyclohexylamide refers to the intermediate, $C_6H_{11}-NH-CO-CH_2-NH_2$.

"Optionally" means that the described circumstance may or may not occur, and that the description includes instances where it occurs and instances where it does not occur. The phrase "optionally substituted" is used herein in conjunction with cycloalkyl, cycloalkyl lower alkyl, phenyl, and phenyl lower alkyl substituents to indicate that the cycloalkyl or phenyl ring may be have on it only hydrogen or, alternatively, may be substituted with one or more of the enumerated radicals as specifically indicated. Likewise, the statement that HX is optionally present means that it can be present, or that the compound can be present in the form of the free base.

"Phenyl lower alkyl" means a group having at least one and up to four methylene groups with an $\omega$-phenyl group. In this instance the carbon chain is linear, not branched. The phenyl group may be unsubstituted, i.e., contain only hydrogen, or it may be substituted with up to 5 substituents of a single functionality or a combination of the several recited substituents. Examples of unsubstituted phenyl lower alkyl are benzyl, phenylethyl, phenylpropyl and phenylbutyl. Examples of substituted phenyl lower alkyl are 4-halophenylalkyl, 2,4-dihalophenylalkyl, 2,4,6-trihalophenylalkyl or 2,3,4,5,6-pentahalo-phenylalkyl wherein halo is as defined below.

In addition, the phenyl group may be substituted with one or more lower alkyl groups such as methyl, ethyl, propyl or the like. One or more lower alkoxy groups may also be substituted on the phenyl ring. In addition, phenyl may be substituted with the radical $-N(R^5)_2$ wherein $R^5$ is lower alkyl.

The term "halo" refers to fluoro, chloro and bromo and iodo.

Perhexylenyl refers to the substituent dicyclohexyl-2-(2-piperidyl)ethane which is disclosed in British Pat. No. 1,025,578.

"Pharmaceutically acceptable acid addition salt" refers to those salts which retain the biological properties and efficacy of the free bases and which are not biologically or otherwise undesirable, formed with inorganic or organic acids. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

A pharmaceutically acceptable excipient is to be broadly understood to include any carrier, analgesic, vitamin, or other substance, such as an inert pharmaceutical additive to facilitate formulation, that is acceptable for administration to a human patient from a toxicity viewpoint and that will not substantially interfere with the administration of the active compound. Suitable excipients include water, aspirin, saline, dextrose, glycerine, ethanol, and the like; pharmaceutical grades of mannitol, lactose, starch, magnesium stearate, sodium saccharin, talcum, cellulose, glucose, sucrose, magnesium carbonate, and the like; polyalkylene glycols such as, for example, propylene glycol; and nontoxic auxiliary substances such as wetting or emulsifying agent, pH buffering agents and the like, for example, sodium acetate, sorbitan monolaurate, triethanolamine sodium acetate, triethanolamine oleate, etc.

Administration and Dosage

Administration of the compounds and salts thereof described herein can be via any of the accepted modes of administration for agents which are cyclic AMP phosphodiesterase inhibitors. These methods include oral, parenteral and otherwise systemic or aerosol forms.

Depending on the intended mode of administration, the compositions used may be in the form of solid, semisolid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain between about 1% and about 99% active ingredient, but preferably contain between about 10% and about 50% active ingredient.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 3,710,795 and 3,773,919.

For systemic administration via suppository, traditional binders and carriers include, e.g. polyalkylene glycols or triglycerides. Such suppositories may be formed from mixtures containing active ingredient in the range of about 0.5% to about 10%; and preferably in the range of from about 1 to about 2%.

The amount of active compound administered will of course, be dependent on the subject being treated, the type and severity of the affliction, the manner of administration and the judgment of the prescribing physician.

In any case, a therapeutically effective amount of the drug either alone or in combination with the various excipients listed above or otherwise known will be administered. For the purposes of this invention, "a therapeutically effective amount" refers to an amount in the range of from about 0.1 to about 25 mg/kg of body weight, and preferably from about 1 to about 10 mg/kg.

Preferred Embodiments

Preferred embodiments of the present invention are compounds, compositions and methods wherein in Formula I: m is 0; Z is O; n is 3 or 4; $R^1$ is an aliphatic radical having more than three carbon atoms and branching at the first or second carbon from the oxygen atom; and $R^2$ is a lower alkyl or aryl radical. Alternative preferred embodiments have like definitions of m, Z, n and $R^2$, but $R^1$ is ethyl.

More preferred embodiments are directed to those compounds described in the preceding paragraph wherein A is $NR^6R^7$ and the $R^6$ and $R^7$ substituents are independently selected from the group consisting of: alkyl of 1 to 6 carbon atoms; cycloalkyl of 3 to 8 carbon atoms; and cycloalkyl lower alkyl of 4 to 12 carbon atoms; and optical isomers of the class of compounds.

Most preferred embodiments are directed to those compounds described above wherein A is $NR^6R^7$ and $R^6$ is alkyl of 1 to 6 carbon atoms and $R^7$ cycloalkyl of 3 to 8 carbon atoms, and optical isomers of the class of compounds. Most particularly preferred are compounds wherein n is 3, $R^6$ is methyl, $R^7$ is cyclohexyl, and the oxybutyramide group is attached to the 6-position of the quinazoline ring.

In addition to the above classes of preferred compounds for use in the compositions and methods of this invention, a presently particularly preferred embodiment uses N-cyclohexyl-N-methyl-4-[2-acetamido-3-(ethoxycarbonylmethyl)-3,4-dihydroquinazolin-6-yl]oxybutyramide, and the pharmaceutically acceptable salts thereof.

The preferred pharmaceutically acceptable salts are HCl, HBr, $H_2SO_4$, $HNO_3$ and $H_3PO_4$.

PREPARATION AND EXAMPLES

Compounds of the present invention can be made by Reaction Scheme I. The starting material (1) is fully taught in U.S. Pat. Nos. 4,490,371 and 4,551,459, issued 12/25/84 and 11/5/85, respectively, and hereby fully incorporated into the instant disclosure by reference. Briefly, the process for preparing the starting material (1), a nitro-aldehyde amide, begins with a hydroxy-2-nitrobenzaldehyde which is reacted with an ω-haloalkylester which serves to introduce the alkyl side chain onto the benzene ring. The ester is then hydrolyzed, converted to the acid chloride and treated with the appropriate secondary amine to form the amide. The starting material (2), an ester or amide derivative of glycine, is prepared in accordance with Reaction Scheme II or III. The nitro-aldehyde amide (1) is reacted with the α-amino acid derivative (2). This reaction is followed by a reduction step, and then by a cyclization step employing a halo cyanogen.

REACTION SCHEME I

Synthesis of compounds of Formula I

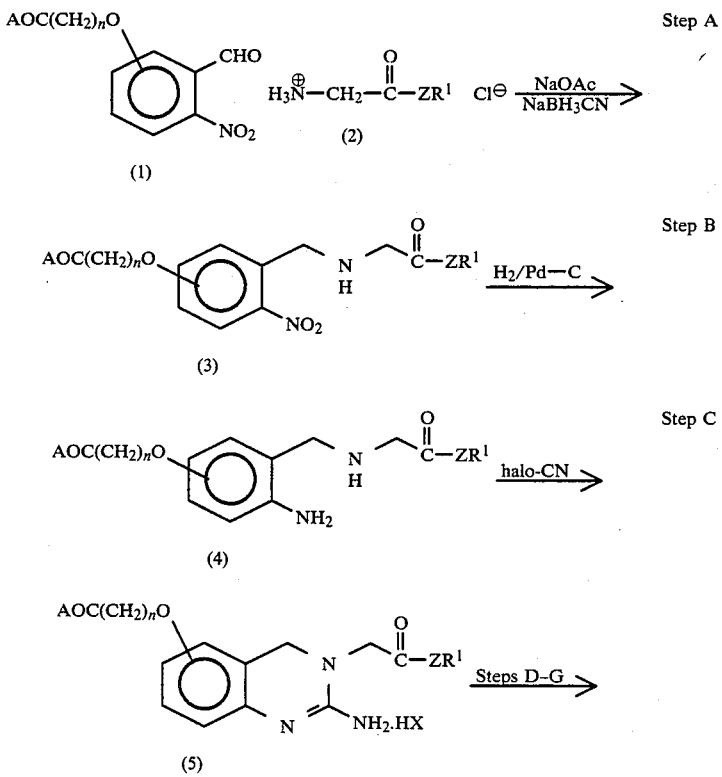

$$\text{AOC(CH}_2)_n\text{O} \underset{\text{(I)}}{\overset{\displaystyle\bigcirc}{\underset{N}{\bigcirc}}}\overset{\displaystyle\text{N}\diagup\text{COZR}^1}{\underset{\text{NHCOYR}^2}{\diagdown}}$$

(I)

$(5) \xrightarrow[\text{base}]{R^2\text{COCl or }(R^2\text{CO})_2\text{O}} (I)\ m=0$    Step D $(5) \xrightarrow[\text{base}]{R^2\text{OCOCl}} (I)\ Y=0,\ m=1$    Step E $(5) \xrightarrow[\text{base}]{R^2\text{N}=\text{C}=\text{O}} (I)\ Y=\text{NH},\ m=1$    Step F $(5) \xrightarrow[\text{base}]{R^2R^4\text{NCOCl}} (I)\ Y=\text{NR}^4,\ m=1$    Step G Regarding the starting material (2), the required ester or amide derivatives of glycine may be prepared by either of two convenient routes set forth below as Reaction Schemes II and III. In Scheme II (Preparations 1 and 2) acylation of an alcohol or primary or secondary amine with an α-halo acetyl chloride is carried out using a tertiary amine base, such as triethylamine or N,N-dimethylaniline in an anhydrous aprotic solvent, such as diethyl ether or tetrahydrofuran. Displacement of the halide with sodium azide, followed by catalytic (or other) reduction and treatment with hydrogen chloride, affords the glycine ester or amide hydrochloride.

REACTION SCHEME II

Preparation of glycine ester and amide hydrochlorides $$X'\!\!-\!\!\overset{O}{\overset{\|}{C}}\!\!-\!\!Cl + HZR^1 \xrightarrow[Et_2O]{Et_3N} X'\!\!-\!\!\overset{O}{\overset{\|}{C}}\!\!-\!\!ZR^1 \xrightarrow[DMF]{NaN_3}$$

$$N_3\!\!-\!\!\overset{O}{\overset{\|}{C}}\!\!-\!\!ZR^1 \xrightarrow[EtOH/HCl]{H_2\ Pd\!\!-\!\!C} H_3\overset{\oplus}{N}\!\!-\!\!\overset{O}{\overset{\|}{C}}\!\!-\!\!ZR^1\ Cl^{\ominus}$$

$X' = Cl, Br, I$
$Z = O\text{ or }NR_2$

Alternatively, as shown in Scheme III (Preparation 3), commercially available N-protected glycine derivatives, such as but not limited to N-Boc-glycine or N-Cbz-glycine, can be converted into activated acylating agents using any of a variety dehydrating reagents, such as carbonyl diimidazole (CDI) or dicyclohexylcarbodiimide (DCC) or the like. The resulting activated glycine derivative is treated in situ with an alcohol or primary or secondary amine to afford the protected ester or amide. Deprotection under the appropriate conditions affords the glycine derivatives as shown in Scheme II.

REACTION SCHEME III

Alternative preparations using N-protected glycine $$\text{MN}\!\!-\!\!\overset{\displaystyle}{\underset{H}{|}}\!\!-\!\!\overset{O}{\overset{\|}{C}}\!\!-\!\!OH \xrightarrow[HZR^1/THF]{CDI\text{ or }DCC}$$

-continued $$\text{MN}\!\!-\!\!\overset{}{\underset{H}{|}}\!\!-\!\!\overset{O}{\overset{\|}{C}}\!\!-\!\!ZR^1 \xrightarrow{\overset{\text{HCl/EtOAc}}{(M=Boc)}} H_3\overset{\oplus}{N}\!\!-\!\!\overset{O}{\overset{\|}{C}}\!\!-\!\!ZR^1\ Cl^{\ominus}$$

$$\xrightarrow[\text{(M = Cbz)}]{H_2/Pd\!\!-\!\!C/EtOH/HCl}$$

$M = (CH_3)_3CO\overset{O}{\overset{\|}{C}}\!\!-$ (Boc) or $PhCH_2O\overset{O}{\overset{\|}{C}}\!\!-$ (Cbz) or other protective group $Z = O\text{ or }NR_2$ Once the starting materials [formulas (1) and (2)] are prepared as outlined above, compounds of formula (1) may be reacted with compounds of formula (2) to yield the compounds of formula (3): the nitroaldehyde amide (1) is condensed by reductive amination (Step A) with an excess of the glycine ester or amide (2), to give the benzylamine (3). Generally, the reaction is carried out at a temperature between about 0° and about 50° C., preferably ambient temperature. A time of between about 0.5 to about 8 hours is sufficient to effect the reaction, though about 2 to about 3 hours is preferable. The reaction is generally carried out in a polar solvent such as an alcohol, for example, methanol, ethanol, propanol, or the like in which the nitroaldehyde-amide and the glycine ester or amide hydrochloride are soluble. It is preferable to add a water-scavenging agent such as molecular sieves in order to remove water generated during the reaction process.

Initially, a reaction mixture is prepared which contains the aldehyde of formula (1), about a two-fold molar amount of the α-amino acid ester of formula (2) as an acid addition salt, and the water scavenging agent. The solution is generally maintained between about 10° to 30° C. for between about 10 minutes and about 3 hours, preferably about 30 minutes, and then there is added a cyanoborohydride reducing agent in a molar amount of about one-half that of the carbonyl compound. The reaction is allowed to proceed at a temperature between about 10° to 30° C., preferably at room temperature for a period of between about 1 to about 6 hours, preferably about 1 to about 2 hours.

While the reaction product may be isolated for characterization, by crystallization or chromatography, for example, such isolation is not necessary. It is most convenient to simply remove precipitated solids, i.e., the molecular sieves and borate salts, by filtration, evaporate the solvent and to take up the residue in an organic solvent. This solution may then be washed with a base and brine to remove impurities, after which the solvent is removed and the resulting residue used directly in the next reaction step.

Reduction of the nitro group (Step B) can be effected by many methods known in the art, but is most conveniently carried out by catalytic hydrogenation. This reaction may be accomplished by conventionally known means. As practiced herein, the residue from the previous reaction step is dissolved in an appropriate solvent such as, for example, a simple alcohol such as methanol or ethanol. A transition metal catalyst which will selectively reduce the nitro group to the amine without affecting the ester and/or amide(s) or the phenyl ring is preferred. A preferred catalyst is a palladium catalyst and most preferably it will be palladium on carbon such as the readily available 10% palladium/carbon catalyst. A small amount of the palladium/carbon catalyst, i.e., between about 0.5 and about 1.5 grams per 100 mmol substrate, will generally be sufficient to effect the reduction. The alcoholic reaction mixture is placed under hydrogen at room temperature and between about 1 to about 3 atmospheres of hydrogen pressure and allowed to proceed until hydrogen uptake has ceased. Isolation of the hydrogenation product is readily accomplished by filtration to remove the catalyst after which the reaction product may be used directly in the following step.

Cyclization of the amine (Step C) is achieved by means of a cyanogen halide, preferably the bromide. A 5 to 10% molar excess of cyanogen halide is added to the solution from the previous reaction. The resulting solution is stirred overnight preferably about 16 hours at temperatures between ambient and reflux, preferably at ambient temperature. The product (5) is isolated by evaporation of the solvent at reduced pressure and at temperatures less than about 40° C., followed by drying at high vacuum and/or recrystallization.

Interconversion of the products of formula (5) can be effected in some instances, as shown in Reaction Scheme IV (preparation 5). The tert-butyl ester is acid labile, affording the free acid upon cleavage. Suitably, anhydrous HBr, preferably in acetic acid can be used in the reaction. (While the acid product is, in principle, available by either alkaline or acid hydrolysis of any ester or amide, the harsh conditions required for such a conversion would afford the ring closed product, disclosed in U.S. Pat. Nos. 4,551,459 and 4,490,371.) Under anhydrous conditions, the free acid can then be converted into another ester of a primary or secondary alcohol by transesterification. This provides two routes to compounds of formula (5) where Z=O.

REACTION SCHEME IV

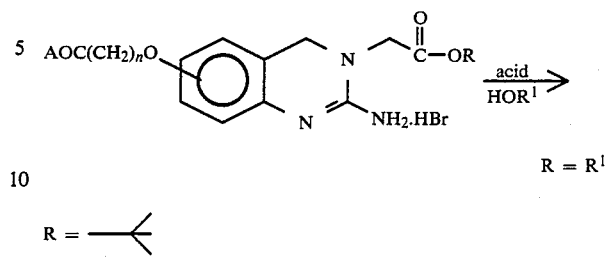

$R = R^1$

Compounds of formula (5) may be converted to the title compounds by four different routes depending on the identity of Y in Formula (I). When m is zero (i.e., Y is nil in Formula I), treatment of (5) as shown in Step D (Example 1) with an activated derivative of an aliphatic or aryl carboxylic acid, such as an acid chloride, acid anhydride, acyl imidazolide or other labile ester, in the presence of one equivalent of base, preferably a tertiary alkylamine, in an aprotic solvent such as dichloromethane, chloroform, tetrahydrofuran or dimethylformamide, at temperatures from 0° to 40° C., affords a compound of Formula I (where Y is nil) after aqueous extractive workups and chromatography over silica gel. Under similar conditions, compounds of formula (5) may be treated with: an activated derivative of a carbonic acid, preferably an alkyl or aryl chloroformate, as shown in Step E, to afford compounds of Formula I when Y is O (oxygen); an aryl or alkyl isocyanate, as shown in Step F, to afford compounds of Formula I where Y is NH; or an activated derivative of a carbonic acid, preferably an aryl or alkyl carbamoyl chloride, to give compounds of Formula I where Y is $NR^4$.

In addition, in the special case where Z is O (oxygen) and $R^1$ is tert-butyl, conversion to other esters may be accomplished by acid-catalysed transesterification, similar to that described above and suitably using HBr as the acid, as shown in Reaction Scheme V. Under acidic conditions but in the absence of $HOR^1$ the corresponding acid of Formula 1 ($Z=O$, $R^1=H$) is prepared (Example 6).

REACTION SCHEME V

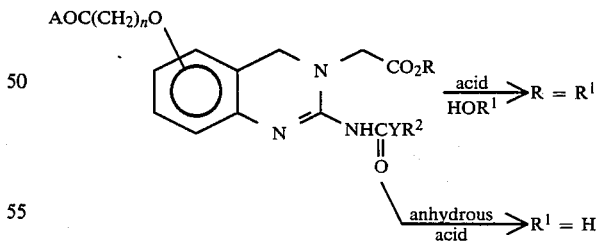

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent, preferably at ambient temperature.

The following Preparations and Examples illustrate how to make the starting materials and compounds of this invention, respectively. They are intended to be illustrative, but not limiting. Preparations 1 through 3 yield the starting material of formula (2). Preparations 4 and 5 illustrate the preparation of compounds of formula (5). Examples 1 through 4 yield the products of Formula I. Example 5 illustrates interconversion to other compounds of Formula I. The remainder of the Examples are directed to formulations and biological data.

PREPARATION 1

Glycine Cyclohexyl Ester Hydrochloride and Related Compounds of Formula (2) Where Z=O Chloroacetyl chloride (40 mL, 500 mmol) was added dropwise to a solution of cyclohexanol (52 mL, 500 mmol) and triethylamine (77 mL, 550 mmol) in diethyl ether cooled to below 5° C. Upon completion of the addition, the mixture was filtered to remove triethylamine hydrochloride. The filtrate was washed twice with 1M HCl and twice with brine, and was then dried over $MgSO_4$, filtered and evaporated to afford cyclohexyl chloroacetate (86.5 g, 490 mmol, 98%) as a colorless liquid, bp 100° C./5 mm. The chloroacetate (79.5 g, 450 mmol) was added dropwise to a suspension of sodium azide (36.6 g, 563 mmol) in dimethylformamide (60 mL) maintained below 20° C. The mixture was stirred at room temperature overnight, and then was poured into water (200 mL), and the solution was extracted with ether (4×200 mL). The combined organic extracts were washed with brine, then dried, filtered and evaporated to yield cyclohexyl azidoacetate (78.4 g, 428 mmol, 95%) as a colorless liquid, b.p. 85°–90° C. (0.1 mm). Catalytic reduction of the azide with hydrogen over 10% palladium on carbon in ethanol afforded cyclohexyl glycinate, treatment of which with dry HCl afforded glycine cyclohexyl ester HCl, m.p. 144°–145° C., in quantitative yield after crystallization from diethyl ether.

Similarly prepared are the following glycine ester hydrochlorides, a few of which are commercially available or previously reported in the literature:
glycine tert-butyl ester HCl;
glycine isopropyl ester HCl;
glycine 2,6-dimethylcyclohexyl ester HCl;
glycine cyclopentyl ester HCl;
glycine cyclohexylmethyl ester HCl;
glycine adamantyl ester HCl;
glycine adamantylmethyl ester HCl;
glycine isobutyl ester HCl;
glycine neopentyl ester HCl;
glycine phenyl ester HCl;
glycine 2,6-dimethylphenyl ester HCl;
glycine 1-phenylethyl ester HCL;
glycine 2,2-dimethyl-3-butyl ester HCL;
glycine 2-phenyl-2-propyl ester HCL;
glycine benzyl ester HCl;
glycine 2,4,6-trimethyl benzyl ester HCL;
glycine trichloromethyl-2-propyl ester HCL; and
glycine 2,4,6-trimethylphenyl ester HCL.

PREPARATION 2

Glycine-N-Cyclohexylamide HCl and Related Compounds of Formula (2) Where $Z=NR^3$ Chloroacetyl chloride (20 mL, 250 mmol) was added dropwise to a chilled solution of cyclohexylamine (57 mL, 500 mmol) in pentane (300 mL). After 1 hour at room temperature, the mixture was diluted with ethyl acetate (500 mL), and was treated with 1M HCl (250 mL). The layers were separated, and the organic extract was washed with 1M HCl, saturated sodium bicarbonate and brine. Evaporation after drying afforded 37 g (211 mmol, 84%) of a white solid, m.p. 108°–109° C. Conversion of the chloroacetamide to the azide and subsequent reduction to the amine and treatment with dry HCl (as in Preparation 1) afforded glycine-N-cyclohexylamide hydrochloride.

Similarly prepared are:
glycine N-isopropylamide hydrochloride;
glycine N,N-dimethylamide hydrochloride;
glycine 1-piperidinylamide hydrochloride;
glycine 4-morpholinylamide hydrochloride;
glycine 4-tert-butylamide hydrochloride; and
glycine anilide hydrochloride.

PREPARATION 3

Glycine Morpholinylamide Hydrochloride and Related Compounds of Formula (2) Where $Z=NR^3$ N,N-Dicyclohexylcarbodiimide (54 g, 265 mmol) was added to a solution of N-Boc glycine (43.8 g, 250 mmol) in ethyl acetate. After stirring at 10° C. for 15 min, morpholine (26 mL, 300 mmol) was added dropwise. The mixture was stirred overnight at room temperature, and then was filtered. The filtrate was washed with water, 1M $NaHSO_4$, aq. $NaHCO_3$ and brine, and then was dried, filtered and concentrated. Crystallization of the residue from ether-ethyl acetate afforded N-t-Boc-glycine morpholinylamide, m.p. 122°–123° C. Treatment with hydrogen chloride in ethyl acetate afforded quantitatively, glycine 4-morpholinylamide hydrochloride, m.p. 218°–220° C. Most esters or amides of Preparations 1 or 2 can be prepared by appropriate modification of this alternative method where convenient.

By using N-Cbz-glycine in place of N-Boc glycine in this Preparation, removal of the protecting group is effected by hydrogenation over Palladium/carbon catalyst to afford the esters of amides previously mentioned, but especially in cases where the ester is acid labile.

PREPARATION 4

N-Cyclohexyl-N-methyl-4-[2-amino-3-(ethoxycarbonylmethyl)-3,4-dihydroquinazolin-6-yl]oxybutyramide Hydrobromide and Related Compounds of Formula (5)

A. Preparation of the Title Compound (5)

Anhydrous sodium acetate (4.1 g, 50 mmol) was added to a warm solution of glycine ethyl ester hydrochloride (8.4 g, 60 mmol) in absolute ethanol (200 mL). The resulting mixture was stirred overnight at room temperature and was then filtered. N-Cyclohexyl-N-methyl-4-(3-formyl-4-nitrophenyl)-oxybutyramide (8.7 g, 25 mmol) was added, followed by sodium cyanoborohydride (0.95 g, 15 mmol) in 30 minutes. After 3 hours, the solution was evaporated, and the residue was partitioned between ethyl acetate and saturated sodium bicarbonate (300 mL each). The organic extract was washed with additional aqueous sodium bicarbonate and with brine, then dried, filtered and evaporated to give the nitroamine as a thick syrup. The crude nitroamine was dissolved in absolute ethanol (100 mL) and was hydrogenated over 10% Pd-C (1.0 g) until uptake ceased, approximately 4 hours. The catalyst was removed by filtration through a Celite pad, and the pad was washed clean with additional absolute ethanol (50 mL). The combined filtrates were treated with cyanogen bromide (3.20 g, 30 mmol), and the resulting solution was stirred at room temperature for 16 hours. Thorough evaporation of the ethanolic solution afforded a quantitative yield of the title compound as an amorphous solid, m.p. 91°–92° C.

B. Preparation of Other Compounds of Formula (5) Using Intermediates of Preparations 1 to 3 Herein By substituting any of the glycine ester or amide hydrochlorides of Preparations 1 to 3 into this procedure, the corresponding 2-amino-3,4-dihydroquinazoline ester or amide hydrobromides are prepared and isolated as the hydrobromide salts:

1. Esters

N-cyclohexyl-N-methyl-4-[2-amino-3-(tert-butyloxycarbonylmethyl)-3,4-dihydroquinazolin-6-yl]oxybutyramide, m.p. 78°–81° C.;

N-cyclohexyl-N-methyl-4-[2-amino-3-(cyclohexyloxycarbonylmethyl)-3,4-dihydroquinazolin-6-yl]oxybutyramide, m.p. 77°–79° C.;

N-cyclohexyl-N-methyl-4-[2-amino-3-(isopropoxycarbonylmethyl)-3,4-dihydroquinazolin-6-yl]oxybutyramide, m.p. 61°–63° C.;

N-cyclohexyl-N-methyl-4-[2-amino-3-(2,6-dimethylcyclohexyloxycarbonylmethyl)-3,4-dihydroquinazolin-6-yl]oxybutyramide;

N-cyclohexyl-N-methyl-4-[2-amino-3-(cyclopentyloxycarbonylmethyl)-3,4-dihydroquinazolin-6-yl]oxybutyramide;

N-cyclohexyl-N-methyl-4-[2-amino-3-(isobutyloxycarbonylmethyl)-3,4-dihydroquinazolin-6-yl]oxybutyramide;

N-cyclohexyl-N-methyl-4-[2-amino-3-(neopentyloxycarbonylmethyl)-3,4-dihydroquinazolin-6-yl]oxybutyramide;

N-cyclohexyl-N-methyl-4-[2-amino-3-(phenoxycarbonylmethyl)-3,4-dihydroquinazolin-6-yl]oxybutyramide;

N-cyclohexyl-N-methyl-4-[2-amino-3-(2,6-dimethylphenoxycarbonylmethyl)-3,4-dihydroquinazolin-6-yl]oxybutyramide;

N-cyclohexyl-N-methyl-4-[2-amino-3-(1-phenethoxycarbonylmethyl)-3,4-dihydroquinazolin-6-yl]oxybutyramide, m.p. 60°–62° C.;

N-cyclohexyl-N-methyl-4-[2-amino-3-(2,2-dimethyl-3-butyloxycarbonylmethyl)-3,4-dihydroquinazolin-6-yl]oxybutyramide, m.p. 45°–48° C.;

N-cyclohexyl-N-methyl-4-[2-amino-3-(2-phenyl-2-propyloxycarbonylmethyl)-3,4-dihydroquinazolin-6-yl]oxybutyramide;

N-cyclohexyl-N-methyl-4-[2-amino-3-(benzyloxycarbonylmethyl)-3,4-dihydroquinazolin-6-yl]oxybutyramide;

N-cyclohexyl-N-methyl-4-[2-amino-3-(2,4,6-trimethylbenzyloxycarbonylmethyl)-3,4-dihydroquinazolin-6-yl]oxybutyramide;

N-cyclohexyl-N-methyl-4-[2-amino-3-(2-trichloromethyl-2-propyloxycarbonylmethyl)-3,4-dihydroquinazolin-6-yl]oxybutyramide; and N-cyclohexyl-N-methyl-4-[2-amino-3-(2,4,6-trimethylphenoxycarbonylmethyl)-3,4-dihydroquinazolin-6-yl]oxybutyramide.

2. Amides

N-cyclohexyl-N-methyl-4-[2-amino-3-(carbamoylmethyl)-3,4-dihydroquinazolin-6-yl]oxybutyramide, m.p. 74°–75° C.;

N-cyclohexyl-N-methyl-4-[2-amino-3-(N-tert-butylcarbamoylmethyl)-3,4-dihydroquinazolin-6-yl]oxybutyramide;

N-cyclohexyl-N-methyl-4-[2-amino-3-(4-morpholinylcarbonylmethyl)-3,4-dihydroquinazolin-6-yl]oxybutyramide, m.p. 50°–52° C.;

N-cyclohexyl-N-methyl-4-[2-amino-3-(1-piperidinylcarbonylmethyl)-3,4-dihydroquinazolin-6-yl]oxybutyramide;

N-cyclohexyl-N-methyl-4-[2-amino-3-N-phenylcarbamoylmethyl)-3,4-dihydroquinazolin-6-yl]oxybutyramide, m.p. 84°–86° C.;

N-cyclohexyl-N-methyl-4-[2-amino-3-N-isopropylcarbamoylmethyl)-3,4-dihydroquinazolin-6-yl]oxybutyramide;

N-cyclohexyl-N-methyl-4-[2-amino-3-N,N-dimethylcarbamoylmethyl)-3,4-dihydroquinazolin-6-yl]oxybutyramide; and N-cyclohexyl-N-methyl-4-[2-amino-3-(N-cyclohexylcarbamoylmethyl)-3,4-dihydroquinazolin-6-yl]oxybutyramide.

C. Preparation of Other Compounds of Formula (5) Using Intermediates Disclosed in U.S. Pat. Nos. 4,551,459 and 4,490,371

By substituting other nitroaldehyde amides of Formula 1 previously disclosed in U.S. Pat. Nos. 4,551,459 and 4,490,371 incorporated herein by reference for N-cyclohexyl-N-methyl-4-(3-formyl-4-nitrophenyl)oxybutyramide incorporated herein by reference, the corresponding 2-amino-3,4-dihydroquinazoline ester or amide hydrobromides are prepared and isolated as the hydrobromide salt:

1. Esters

N-hexyl-N-methyl-4-[2-amino-3-(tert-butyloxycarbonylmethyl)-3,4-dihydroquinazolin-6-yl]oxybutyramide;

N,N-dimethyl-4-[2-amino-3-(cyclohexyloxycarbonylmethyl)-3,4-dihydroquinazolin-6-yl]oxybutyramide;

N-ethyl-N-methyl-4-[2-amino-3-(isopropyloxycarbonylmethyl)-3,4-dihydroquinazolin-6-yl]oxybutyramide;

N-pentyl-N-methyl-4-[2-amino-3-(2,6-dimethylcyclohexyloxycarbonylmethyl)-3,4-dihydroquinazolin-6-yl]oxybutyramide;

N,N-dihexyl-4-[2-amino-3-(cyclopentyloxycarbonylmethyl)-3,4-dihydroquinazolin-6-yl]oxybutyramide;

N,N-dipentyl-4-[2-amino-3-(isobutyloxycarbonylmethyl)-3,4-dihydroquinazolin-6-yl]oxybutyramide;

N-cyclohexyl-N-n-hexyl-4-[2-amino-3-(neopentyloxycarbonylmethyl)-3,4-dihydroquinazolin-6-yl]oxybutyramide;

N-cyclopentyl-N-methyl-4-[2-amino-3-(2-phenoxycarbonylmethyl)-3,4-dihydroquinazolin6-yl]oxybutyramide;

N-cyclopropylmethyl-N-methyl-4-[2-amino-3-(2,6-dimethylphenoxycarbonylmethyl)-3,4-dihydroquinazolin-6-yl]oxybutyramide;
N-cycloheptyl-N-methyl-4-[2-amino-3-(1-phenethoxycarbonylmethyl)-3,4-dihydroquinazolin-6-yl]oxybutyramide;
N-cyclopentylbutyl-N-methyl-4-[2-amino-3-(2,2-dimethyl-3-butyloxycarbonylmethyl)-3,4-dihydroquinazolin-6-yl]oxybutyramide;
N-cyclopentylmethyl-N-methyl-4-[2-amino-3-(2-phenyl-2-propyloxycarbonylmethyl)-3,4-dihydroquinazolin-6-yl]oxybutyramide;
N-cyclopentyl-N-butyl-4-[2-amino-3-(benzyloxycarbonylmethyl)-3,4-dihydroquinazolin-6-yl]oxybutyramide;
N,N-dicyclohexyl-4-[2-amino-3-(2,4,6-trimethylbenzyloxycarbonylmethyl)-3,4-dihydroquinazolin-6-yl]oxybutyramide;
N-phenyl-N-methyl-4-[2-amino-3-(2-trichloromethyl-2-propyloxycarbonylmethyl)-3,4-dihydroquinazolin-6-yl]oxybutyramide;
N-phenyl-N-hexyl-4-[2-amino-3-(2,4,6-trimethylphenoxycarbonylmethyl)-3,4-dihydroquinazolin-6-yl]oxybutyramide;
morpholinyl-4-[2-amino-3-(methoxycarbonylmethyl)-3,4-dihydroquinazolin-7-yl]oxybutyramide;
piperidinyl-4-[2-amino-3-(benzyloxycarbonylmethyl)-3,4-dihydroquinazolin-7-yl]oxybutyramide;
pyrrolidinyl-4-[2-amino-3-(tert-butyloxycarbonylmethyl)-3,4-dihydroquinazolin-7-yl]oxybutyramide;
N-methylpiperazinyl-4-[2-amino-3-(neopentyloxycarbonylmethyl)-3,4-dihydroquinazolin-7-yl]oxybutyramide;
tetrahydroquinolinyl-4-[2-amino-3-(isobutyloxycarbonylmethyl)-3,4-dihydroquinazolin-7-yl]oxybutyramide;
tetrahydroisoquinolinyl-4-[2-amino-3-(2-chlorophenyloxycarbonylmethyl)-3,4-dihydroquinazolin-7-yl]oxybutyramide;
indolinyl-4-[2-amino-3-(2-dimethylaminophenoxycarbonylmethyl)-3,4-dihydroquinazolin-7-yl]oxybutyramide;
(±)-decahydroquinolinyl-4-[2-amino-3-(isopropyloxycarbonylmethyl)-3,4-dihydroquinazolin-7-yl]oxybutyramide;
N-cyclohexyl-N-methyl-4-[2-amino-3-(benzyloxycarbonylmethyl)-3,4-dihydroquinazolin-8-yl]oxybutyramide;
N-cyclohexyl-N-n-hexyl-4-[2-amino-3-(neopentyloxycarbonylmethyl)-3,4-dihydroquinazolin-8-yl]oxybutyramide;
N-phenyl-N-methyl-4-[2-amino-3-(isobutyloxycarbonylmethyl)-3,4-dihydroquinazolin-8-yl]oxybutyramide;
N-benzyl-N-methyl-4-[2-amino-3-(2-chlorophenoxycarbonylmethyl)-3,4-dihydroquinazolin-8-yl]oxybutyramide;
N,N-dibenzyl-4-[2-amino-3-(2-dimethylaminophenoxycarbonylmethyl)-3,4-dihydroquinazolin-8-yl]oxybutyramide;
N,N-dicyclohexyl-4-[2-amino-3-(isopropyloxycarbonylmethyl)-3,4-dihydroquinazolin-8-yl]oxybutyramide;
(±)-decahydroquinolinyl-4-[2-amino-3-(benzyloxycarbonylmethyl)-3,4-dihydroquinazolin-5-yl]oxybutyramide;
N-phenyl-N-methyl-4-[2-amino-3-(neopentyloxycarbonylmethyl)-3,4-dihydroquinazolin-5-yl]oxybutyramide;
N-cyclohexyl-N-methyl-4-[2-amino-3-(isobutyloxycarbonylmethyl)-3,4-dihydroquinazolin-5-yl]oxybutyramide;
N-benzyl-N-methyl-4-[2-amino-3-(2-chlorophenoxyoxycarbonylmethyl)-3,4-dihydroquinazolin-5-yl]oxybutyramide;
N,N-dibenzyl-4-[2-amino-3-(2-dimethylaminophenoxyoxycarbonylmethyl)-3,4-dihydroquinazolin-5-yl]oxybutyramide; and
N,N-dicyclohexyl-4-[2-amino-3-(isopropyloxycarbonylmethyl)-3,4-dihydroquinazolin-5-yl]oxybutyramide.

2. Amides

N-hexyl-N-methyl-4-[2-amino-3-(carbamoylmethyl)-3,4-dihydroquinazolin-6-yl]oxybutyramide;
N,N-dimethyl-4-[2-amino-3-(N-tert-butylcarbamoylmethyl)-3,4-dihydroquinazolin-6-yl]oxybutyramide;
N-ethyl-N-methyl-4-[2-amino-3-(4-morpholinylcarbamoylmethyl)-3,4-dihydroquinazolin-6-yl]oxybutyramide;
N-pentyl-N-methyl-4-[2-amino-3-(1-piperidinylcarbamoylmethyl)-3,4-dihydroquinazolin-6-yl]oxybutyramide;
N,N-dihexyl-4-[2-amino-3-(N-phenylcarbamoylmethyl)-3,4-dihydroquinazolin-6-yl]oxybutyramide;
N,N-dipentyl-4-[2-amino-3-N-isopropylcarbamoylmethyl)-3,4-dihydroquinazolin-6-yl]oxybutyramide;
N-cyclohexyl-N-n-hexyl-4-[2-amino-3-N,N-dimethylcarbamoylmethyl)-3,4-dihydroquinazolin-6-yl]oxybutyramide;
N-cycloheptyl-N-methyl-4-[2-amino-3-((N-cyclohexylcarbamoylmethyl)-3,4-dihydroquinazolin-6-yl]oxybutyramide;
morpholinyl-4-[2-amino-3-(N-methylcarbamoylmethyl)-3,4-dihydroquinazolin-7-yl]oxybutyramide;
piperidinyl-4-[2-amino-3-(N-benzylcarbamoylmethyl)-3,4-dihydroquinazolin-7-yl]oxybutyramide;
pyrrolidinyl-4-[2-amino-3-(N-tert-butylcarbamoylmethyl)-3,4-dihydroquinazolin-7-yl]oxybutyramide;
N-methylpiperazinyl-4-[2-amino-3-(N-neopentyl-N-methylcarbamoylmethyl)-3,4-dihydroquinazolin-7-yl]oxybutyramide;
tetrahydroquinolinyl-4-[2-amino-3-(N-propyl-N-isobutylcarbamoylmethyl)-3,4-dihydroquinazolin-7-yl]oxybutyramide;
tetrahydroisoquinolinyl-4-[2-amino-3-(N-octyl-N-2-chlorophenylcarbamoylmethyl)-3,4-dihydroquinazolin-7-yl]oxybutyramide;
indolinyl-4-[2-amino-3-(N-2-dimethylaminophenylcarbamoylmethyl)-3,4-dihydroquinazolin-7-yl]oxybutyramide;
(±)-decahydroquinolinyl-4-[2-amino-3-(N-cyclohexyl-N-isopropylcarbamoylmethyl)-3,4-dihydroquinazolin-7-yl]oxybutyramide;
N-cyclohexyl-N-methyl-4-[2-amino-3-(N-benzylcarbamoylmethyl)-3,4-dihydroquinazolin-8-yl]oxybutyramide;
N-cyclohexyl-N-n-hexyl-4-[2-amino-3-(N-neopentylcarbamoylmethyl)-3,4-dihydroquinazolin-8-yl]oxybutyramide;
N-phenyl-N-methyl-4-[2-amino-3-(N-isobutylcarbamoylmethyl)-3,4-dihydroquinazolin-8-yl]oxybutyramide;

N-benzyl-N-methyl-4-[2-amino-3-(N-2-chlorophenyl-carbamoylmethyl)-3,4-dihydroquinazolin-8-yl]ox-ybutyramide;

N,N-dibenzyl-4-[2-amino-3-(N-2-dimethylamino-phenylcarbamoylmethyl)-3,4-dihydroquinazolin-8-yl]oxybutyramide;

N,N-dicyclohexyl-4-[2-amino-3-(N-isopropylcar-bamoylmethyl)-3,4-dihydroquinazolin-8-yl]ox-ybutyramide;

(±)-decahydroquinolinyl-4-[2-amino-3-(N-benzylox-ycarbonylmethyl)-3,4-dihydroquinazolin-5-yl]ox-ybutyramide;

N-phenyl-N-methyl-4-[2-amino-3-(N-neopentylcar-bamoylmethyl)-3,4-dihydroquinazolin-5-yl]ox-ybutyramide;

N-cyclohexyl-N-methyl-4-[2-amino-3-(N,N-di-isobutyl-carbamoylmethyl)-3,4-dihydroquinazolin-5-yl]ox-ybutyramide;

N-benzyl-N-methyl-4-[2-amino-3-(N-2-chlorophenyl-carbamoylmethyl)-3,4-dihydroquinazolin-5-yl]ox-ybutyramide;

N,N-dibenzyl-4-[2-amino-3-(N-2-dimethylamino-phenylcarbamoylmethyl)-3,4-dihydroquinazolin-5-yl]oxybutyramide; and N,N-dicyclohexyl-4-[2-amino-3-(N-isopropylcar-bamoylmethyl)-3,4-dihydroquinazolin-5-yl]ox-ybutyramide.

PREPARATION 5

Formula (5) Ester Interconversion

A suspension of the tert-butyl ester prepared in Preparation 4, in ethanol, was treated with dry HBr in ethanol (2 mL/g). After stirring at ambient temperature overnight, the resulting solution was thoroughly evaporated to afford the ethyl ester hydrobromide of Preparation 4. Similarly, by substituting any non-acid sensitive alcohol for ethanol, the corresponding esters of Preparation 4 can be prepared.

EXAMPLE 1

N-Cyclohexyl-N-Methyl-4-[2-acetamido-3-(2,2-dimethyl-3-butyloxycarbonylmethyl)-3,4-dihydroquinazolin-6-yl]oxybutyramide A. Preparation of the Title Compound by Step D A solution of N-cyclohexyl-N-methyl-4-[2-amino-3-(2,2-dimethyl-3-butyloxycarbonylmethyl)-3,4-dihy-droquinazolin-6-yl]oxybutyramide hydrobromide (14.2 g, 25 mmol) dissolved in dichloromethane (50 mL) and acetic anhydride (10 mL) was treated dropwise with triethylamine. After stirring overnight at room temperature, the mixture was evaporated, and the resulting residue was dissolved in ethyl acetate. The organic layer was washed with water, half-saturated aqueous sodium bicarbonate and brine, and then was dried, filtered and evaporated. Chromatography of the residue over silica gel (3:1 dichloromethane-ethyl acetate as eluant) afforded the title compound as an amorphous foam.

B. Preparation of Other Compounds of Formula I (m is 0) from Compounds of Formula 5 (from Preparation 4)

By substitution of the esters (Z=O) or amides (Z=NH, NR³) of Preparation 4 for the above cited starting material of formula (5), and by optional substitution of other acid anhydrides or acid chlorides for acetic anhydride, the following compounds of Formula I may be prepared:

1. Esters

N-cyclohexyl-N-methyl-4-[2-acetamido-3-(ethoxycar-bonylmethyl)-3,4-dihydroquinazolin-6-yl]oxybutyra-mide;

N-cyclohexyl-N-methyl-4-[2-propionylamino-3-(ethox-ycarbonylmethyl)-3,4-dihydroquinazolin-6-yl]ox-ybutyramide;

N-cyclohexyl-N-methyl-4-[2-isobutyrylamino-3-(ethox-ycarbonylmethyl)-3,4-dihydroquinazolin-6-yl]ox-ybutyramide;

N-cyclohexyl-N-methyl-4-[2-pivaloylamino-3-(ethox-ycarbonylmethyl)-3,4-dihydroquinazolin-6-yl]ox-ybutyramide;

N-cyclohexyl-N-methyl-4-[2-benzamido-3-(ethoxycar-bonylmethyl)-3,4-dihydroquinazolin-6-yl]oxybutyra-mide;

N-cyclohexyl-N-methyl-4-[2-(4-methoxy)benzamido-3-(ethoxycarbonylmethyl)-3,4-dihydroquinazolin-6-yl]oxybutyramide;

N-cyclohexyl-N-methyl-4-[2-(4-chloro)benzamido-3-(ethoxycarbonylmethyl)-3,4-dihydroquinazolin-6-yl]oxybutyramide;

N-cyclohexyl-N-methyl-4-[2-(4-N,N-dimethylamino)-benzamido-3-(ethoxycarbonylmethyl)-3,4-dihy-droquinazolin-6-yl]oxybutyramide;

N-cyclohexyl-N-methyl-4-[2-cyclohexylcar-bonylamino-3-(ethoxycarbonylmethyl)-3,4-dihy-droquinazolin-6-yl]oxybutyramide;

N-cyclohexyl-N-methyl-4-[2-phenylacetamido-3-(ethoxycarbonylmethyl)-3,4-dihydroquinazolin-6-yl]oxybutyramide;

N-cyclohexyl-N-methyl-4-[2-(4-methoxy)-phenylacetamido-3-(ethoxycarbonylmethyl)-3,4-dihydroquinazolin-6-yl]oxybutyramide;

N-cyclohexyl-N-methyl-4-[2-(2-cyclohexyl)acetamido-3-(ethoxycarbonylmethyl)-3,4-dihydroquinazolin-6-yl]oxybutyramide;

N-cyclohexyl-N-methyl-4-[2-acetamido-3-(tert-butyloxycarbonylmethyl)-3,4-dihydroquinazolin-6-yl]oxybutyramide;

N-cyclohexyl-N-methyl-4-[2-acetamido-3-(cyclohex-yloxycarbonylmethyl)-3,4-dihydroquinazolin-6-yl]oxybutyramide N-cyclohexyl-N-methyl-4-[2-acetamido-3-(isopropox-ycarbonylmethyl)-3,4-dihydroquinazolin-6-yl]ox-ybutyramide;

N-cyclohexyl-N-methyl-4-[2-acetamido-3-(2,6-dime-thylcyclohexyloxycarbonylmethyl)-3,4-dihy-droquinazolin-6-yl]oxybutyramide;

N-cyclohexyl-N-methyl-4-[2-N-propionylamino-3-(cy-clopentyloxycarbonylmethyl)-3,4-dihydroquinazo-lin-6-yl]oxybutyramide;

N-cyclohexyl-N-methyl-4-[2-N-propionylamino-3-(isobutyloxycarbonylmethyl)-3,4-dihydroquinazolin-6-yl]oxybutyramide;

N-cyclohexyl-N-methyl-4-[2-N-isobutyrylamino-3-(neopentyloxycarbonylmethyl)-3,4-dihydroquinazo-lin-6-yl]oxybutyramide;

N-cyclohexyl-N-methyl-4-[2-benzamido-3-(phenox-ycarbonylmethyl)-3,4-dihydroquinazolin-6-yl]ox-ybutyramide;

N-cyclohexyl-N-methyl-4-[2-benzamido-3-(2,6-dimeth-yl-phenoxycarbonylmethyl)-3,4-dihydroquinazolin-6-yl]oxybutyramide;

N-cyclohexyl-N-methyl-4-[2-cyclohexylacetamido-3-(1-phenethoxycarbonylmethyl)-3,4-dihydroquinazolin-6-yl]oxybutyramide;
N-cyclohexyl-N-methyl-4-[2-cyclohexylacetamido-3-(2,2-dimethyl-3-butyloxycarbonylmethyl)-3,4-dihydroquinazolin-6-yl]oxybutyramide;
N-cyclohexyl-N-methyl-4-[2-phenylacetamido-3-(2-phenyl-2-propyl-oxycarbonylmethyl)-3,4-dihydroquinazolin-6-yl]oxybutyramide;
N-cyclohexyl-N-methyl-4-[2-(4-methoxybenzamido-3-(benzyloxycarbonylmethyl)-3,4-dihydroquinazolin-6-yl]oxybutyramide;
N-cyclohexyl-N-methyl-4-[2-(4-methoxybenzamido)-3-(2,4,6-trimethylbenzyloxycarbonylmethyl)-3,4-dihydroquinazolin-6-yl]oxybutyramide;
N-cyclohexyl-N-methyl-4-[2-(4-dimethylaminobenzamido]-3-(2-trichloromethyl-2-propyloxycarbonylmethyl)-3,4-dihydroquinazolin-6-yl]oxybutyramide;
N-cyclohexyl-N-methyl-4-[2-(4-chlorophenylacetamido)-3-(2,4,6-trimethylphenoxycarbonylmethyl)-3,4-dihydroquinazolin-6-yl]oxybutyramide;
N-hexyl-N-methyl-4-[2-acetamido-3-(tert-butyloxycarbonylmethyl)-3,4-dihydroquinazolin-6-yl]oxybutyramide;
N,N-dimethyl-4-[2-acetamido-3-(cyclohexyloxycarbonylmethyl)-3,4-dihydroquinazolin-6-yl]oxybutyramide;
N-ethyl-N-methyl-4-[2-acetamido-3-(isopropyloxycarbonylmethyl)-3,4-dihydroquinazolin-6-yl]oxybutyramide;
N-pentyl-N-methyl-4-[2-acetamido-3-(2,6-dimethylcyclohexyloxycarbonylmethyl)-3,4-dihydroquinazolin-6-yl]oxybutyramide;
N,N-dihexyl-4-[2-N-propionylamino-3-(cyclopentyloxycarbonylmethyl)-3,4-dihydroquinazolin-6-yl]oxybutyramide;
N,N-dipentyl-4-[2-N-propionylamino-3-(isobutyloxycarbonylmethyl)-3,4-dihydroquinazolin-6-yl]oxybutyramide;
N-cyclohexyl-N-n-hexyl-4-[2-N-isobutyrylamino-3-(neopentyloxycarbonylmethyl)-3,4-dihydroquinazolin-6-yl]oxybutyramide;
N-cyclopentyl-N-methyl-4-[2-N-isobutyrylamino-3-(2-phenoxycarbonylmethyl)-3,4-dihydroquinazolin6-yl]oxybutyramide;
N-cyclopropylmethyl-N-methyl-4-[2-benzamido-3-(2,6-dimethylphenoxycarbonylmethyl)-3,4-dihydroquinazolin-6-yl]oxybutyramide;
N-cycloheptyl-N-methyl-4-[2-benzamido-3-(1-phenethoxycarbonylmethyl)-3,4-dihydroquinazolin-6-yl]oxybutyramide;
N-cyclopentylbutyl-N-methyl-4-[2-N-cyclohexylacetylamido-3-(2,2-dimethyl-3-butyloxycarbonylmethyl)-3,4-dihydroquinazolin-6-yl]oxybutyramide;
N-cyclopentylmethyl-N-methyl-4-[2-N-cyclohexylacetylamido-3-(2-phenyl-2-propyloxycarbonylmethyl)-3,4-dihydroquinazolin-6-yl]oxybutyramide;
N-cyclopentyl-N-butyl-4-[2-phenylacetylamido-3-(benzyloxycarbonylmethyl)-3,4-dihydroquinazolin-6-yl]oxybutyramide;
N,N-dicyclohexyl-4-[2-(4-methoxybenzamido)-3-(2,4,6-trimethylbenzyloxycarbonylmethyl)-3,4-dihydroquinazolin-6-yl]oxybutyramide;
N-phenyl-N-methyl-4-[2-(4-dimethylaminobenzamido)-3-(2-trichloromethyl-2-propyloxycarbonylmethyl)-3,4-dihydroquinazolin-6-yl]oxybutyramide;
N-phenyl-N-hexyl-4-[2-(4-chlorophenylacetamido)-3-(2,4,6-trimethylphenoxycarbonylmethyl)-3,4-dihydroquinazolin-6-yl]oxybutyramide;
morpholinyl-4-[2-acetamido-3-(methoxycarbonylmethyl)-3,4-dihydroquinazolin-7-yl]oxybutyramide;
piperidinyl-4-[2-acetamido-3-(benzyloxycarbonylmethyl)-3,4-dihydroquinazolin-7-yl]oxybutyramide;
pyrrolidinyl-4-[2-acetamido-3-(tert-butyloxycarbonylmethyl)-3,4-dihydroquinazolin-7-yl]oxybutyramide;
N-methylpiperazinyl-4-[2-acetamido-3-(neopentyloxycarbonylmethyl)-3,4-dihydroquinazolin-7-yl]oxybutyramide;
tetrahydroquinolinyl-4-[2-acetamido-3-(isobutyloxycarbonylmethyl)-3,4-dihydroquinazolin-7-yl]oxybutyramide;
tetrahydroisoquinolinyl-4-[2-benzamido-3-(2-chlorophenyloxycarbonylmethyl)-3,4-dihydroquinazolin-7-yl]oxybutyramide;
indolinyl-4-[2-benzamido-3-(2-dimethylaminophenoxycarbonylmethyl)-3,4-dihydroquinazolin-7-yl]oxybutyramide;
(±)-decahydroquinolinyl-4-[2-benzamido-3-(isopropyloxycarbonylmethyl)-3,4-dihydroquinazolin-7-yl]oxybutyramide;
N-cyclohexyl-N-methyl-4-[2-benzamido-3-(benzyloxycarbonylmethyl)-3,4-dihydroquinazolin-8-yl]oxybutyramide;
N-cyclohexyl-N-n-hexyl-4-[2-benzamido-3-(neopentyloxycarbonylmethyl)-3,4-dihydroquinazolin-8-yl]oxybutyramide;
N-phenyl-N-methyl-4-[2-phenylacetamido-3-(isobutyloxycarbonylmethyl)-3,4-dihydroquinazolin-8-yl]oxybutyramide;
N-benzyl-N-methyl-4-[2-phenylacetamido-3-(2-chlorophenoxycarbonylmethyl)-3,4-dihydroquinazolin-8-yl]-oxybutyramide;
N,N-dibenzyl-4-[2-phenylacetamido-3-(2-dimethylaminophenoxycarbonylmethyl)-3,4-dihydroquinazolin-8-yl]oxybutyramide;
N,N-dicyclohexyl-4-[2-phenylacetamido-3-(isopropyloxycarbonylmethyl)-3,4-dihydroquinazolin-8-yl]oxybutyramide;
(±)-decahydroquinolinyl-4-[2-phenylacetamido-3-(benzyloxycarbonylmethyl)-3,4-dihydroquinazolin-5-yl]oxybutyramide;
N-phenyl-N-methyl-4-[2-N-propionylamino-3-(neopentyloxycarbonylmethyl)-3,4-dihydroquinazolin-5-yl]oxybutyramide;
N-cyclohexyl-N-methyl-4-[2-N-isobutyrylamino-3-(isobutyloxycarbonylmethyl)-3,4-dihydroquinazolin-5-yl]oxybutyramide;
N-benzyl-N-methyl-4-[2-(4-methoxybenzamido)-3-(2-chlorophenoxycarbonylmethyl)-3,4-dihydroquinazolin-5-yl]-oxybutyramide;
N,N-dibenzyl-4-[2-(4-dimethylaminobenzamido)-3-(2-dimethylaminophenoxycarbonylmethyl)-3,4-dihydroquinazolin-5-yl]oxybutyramide; and
N,N-dicyclohexyl-4-[2-(4-chlorophenylacetamido)-3-(isopropyloxycarbonylmethyl)-3,4-dihydroquinazolin-5-yl]oxybutyramide.

2. Amides

N-cyclohexyl-N-methyl-4-[2-acetamido-3-(carbamoylmethyl)-3,4-dihydroquinazolin-6-yl]oxybutyramide;
N-cyclohexyl-N-methyl-4-[2-acetamido-3-(N-tert-butylcarbamoylmethyl)-3,4-dihydroquinazolin-6-yl]oxybutyramide;

N-cyclohexyl-N-methyl-4-[2-benzamido-3-(4-morpholinylcarbonylmethyl)-3,4-dihydroquinazolin-6-yl]oxybutyramide;
N-cyclohexyl-N-methyl-4-[2-phenylacetamido-3-(1-piperidinylcarbonylmethyl)-3,4-dihydroquinazolin-6-yl]oxybutyramide;
N-cyclohexyl-N-methyl-4-[2-(4-dimethylaminobenzamido)-3-N-phenylcarbamoylmethyl)-3,4-dihydroquinazolin-6-yl]oxybutyramide;
N-cyclohexyl-N-methyl-4-[2-(4-chlorophenylacetamido)-3-N-isopropylcarbamoylmethyl)-3,4-dihydroquinazolin-6-yl]oxybutyramide;
N-cyclohexyl-N-methyl-4-[2-(4-methoxybenzamido)-3-N,N-dimethylcarbamoylmethyl)-3,4-dihydroquinazolin-6-yl]oxybutyramide;
N-cyclohexyl-N-methyl-4-[2-phenylacetamido-3-(N-cyclohexylcarbamoylmethyl)-3,4-dihydroquinazolin-6-yl]oxybutyramide;
N-hexyl-N-methyl-4-[2-acetamido-3-(carbamoylmethyl)-3,4-dihydroquinazolin-6-yl]oxybutyramide;
N,N-dimethyl-4-[2-acetamido-3-(N-tert-butylcarbamoylmethyl)-3,4-dihydroquinazolin-6-yl]oxybutyramide;
N-ethyl-N-methyl-4-[2-benzamido-3-(4-morpholinylcarbamoylmethyl)-3,4-dihydroquinazolin-6-yl]oxybutyramide;
N-pentyl-N-methyl-4-[2-phenylacetamido-3-(1-piperidinylcarbamoylmethyl)-3,4-dihydroquinazolin-6-yl]oxybutyramide;
N,N-dihexyl-4-[2-(4-dimethylaminobenzamido)-3-(N-phenylcarbamoylmethyl)-3,4-dihydroquinazolin-6-yl]oxybutyramide;
N,N-dipentyl-4-[2-acetamido-3-N-isopropylcarbamoylmethyl)-3,4-dihydroquinazolin-6-yl]oxybutyramide;
N-cyclohexyl-N-n-hexyl-4-[2-acetamido-3-N,N-dimethylcarbamoylmethyl)-3,4-dihydroquinazolin-6-yl]oxybutyramide;
N-cyclopentyl-N-methyl-4-[2-cyclohexylacetamido-3-(N-cyclohexylcarbamoylmethyl)-3,4-dihydroquinazolin-6-yl]oxybutyramide;
morpholinyl-4-[2-acetamido-3-(N-methylcarbamoylmethyl)3,4-dihydroquinazolin-7-yl]oxybutyramide;
piperidinyl-4-[2-acetamido-3-(N-benzylcarbamoylmethyl)3,4-dihydroquinazolin-7-yl]oxybutyramide;
pyrrolidinyl-4-[2-acetamido-3-(N-tert-butylcarbamoylmethyl)-3,4-dihydroquinazolin-7-yl]oxybutyramide;
N-methylpiperazinyl-4-[2-acetamido-3-(N-neopentylmethylcarbamoylmethyl)-3,4-dihydroquinazolin-7-yl]oxybutyramide;
tetrahydroquinolinyl-4-[2-acetamido-3-(N-propyl-N-isobutylcarbamoylmethyl)-3,4-dihydroquinazolin-7-yl]oxybutyramide;
tetrahydroisoquinolinyl-4-[2-benzamido-3-(N-octyl-N-2-chlorophenylcarbamoylmethyl)-3,4-dihydroquinazolin-7-yl]oxybutyramide;
indolinyl-4-[2-benzamido-3-(N-2-dimethylaminophenylcarbamoylmethyl)-3,4-dihydroquinazolin-7-yl]oxybutyramide;
(±)-decahydroquinolinyl-4-[2-benzamido-3-(N-cyclohexyl-N-isopropylcarbamoylmethyl)-3,4-dihydroquinazolin-7-yl]oxybutyramide;
N-cyclohexyl-N-methyl-4-[2-benzamido-3-(N-benzylcarbamoyl-methyl)-3,4-dihydroquinazolin-8-yl]oxybutyramide;
N-cyclohexyl-N-n-hexyl-4-[2-benzamido-3-(N-neopentylcarbamoylmethyl)-3,4-dihydroquinazolin-8-yl]oxybutyramide;
N-phenyl-N-methyl-4-[2-phenylacetamido-3-(N-isobutylcarbamoylmethyl)-3,4-dihydroquinazolin-8-yl]oxybutyramide;
N-benzyl-N-methyl-4-[2-phenylacetamido-3-(N-2-chlorophenylcarbamoylmethyl)-3,4-dihydroquinazolin-8-yl]oxybutyramide;
N,N-dibenzyl-4-[2-phenylacetamido-3-(N-2-dimethylaminophenylcarbamoylmethyl)-3,4-dihydroquinazolin-8-yl]oxybutyramide;
N,N-dicyclohexyl-4-[2-phenylacetamido-3-(N-isopropylcarbamoylmethyl)-3,4-dihydroquinazolin-8-yl]oxybutyramide;
(±)-decahydroquinolinyl-4-[2-phenylacetamido-3-(N-benzyloxycarbonylmethyl)-3,4-dihydroquinazolin-5-yl]oxybutyramide;
N-phenyl-N-methyl-4-[2-N-propionylamino-3-(N-neopentylcarbamoylmethyl)-3,4-dihydroquinazolin-5-yl]oxybutyramide;
N-cyclohexyl-N-methyl-4-[2-N-isobutyrylamino-3-(N,N-di-isobutylcarbamoylmethyl)-3,4-dihydroquinazolin-5-yl]oxybutyramide;
N-benzyl-N-methyl-4-[2-(4-methoxybenzamido)-3-(N-2-chlorophenylcarbamoylmethyl)-3,4-dihydroquinazolin-5-yl]oxybutyramide;
N,N-dibenzyl-4-[2-(4-dimethylaminobenzamido)-3-(N-2-dimethylaminophenylcarbamoylmethyl)-3,4-dihydroquinazolin-5-yl]oxybutyramide; and
N,N-dicyclohexyl-4-[2-(4-chlorophenylacetylamino)-3-(N-isopropylcarbamoylmethyl)-3,4-dihydroquinazolin-5-yl]oxybutyramide.

EXAMPLE 2

N-Cyclohexyl-N-methyl-4-[2-phenoxycarbonylamino-3-(cyclohexyloxycarbonylmethyl)-3,4-dihydroquinazolin-6-yl]oxybutyramide A. Preparation of the Title Compound by Step E A solution of N-cyclohexyl-N-methyl-4-[2-amino-3-(cyclohexyloxycarbonylmethyl)-3,4-dihydroquinazolin-6-yl]oxybutyramide hydrobromide (5.65 g, 10 mmol) and phenyl chloroformate (1.5 mL) dissolved in dichloromethane (25 mL) was treated dropwise with triethylamine (3.5 mL, 25 mmol). After stirring overnight at room temperature, workup as in Example 1 afforded the title compound as a crystalline solid from ether after silica gel chromatography.

B. Preparation of Other Compounds of Formula I (m=1, Y=Oxygen) from Compounds of Formula 5 (from Preparation 4)

By substitution of the esters (Z=O) or amides (Z=NH, NR³) of Preparation 4 for the above cited starting material of formula (5), and by optional substitution of other chloroformates for phenyl chloroformate, the following compounds of Formula I may be prepared:

1. Esters

P0   N-cyclohexyl-N-methyl-4-[2-methoxycarbonylamino-3-(ethoxycarbonylmethyl)-3,4-dihydroquinazolin-6-yl]oxybutyramide;
N-cyclohexyl-N-methyl-4-[2-ethoxycarbonylamino-3-(ethoxycarbonylmethyl)-3,4-dihydroquinazolin-6-yl]oxybutyramide;
N-cyclohexyl-N-methyl-4-[2-propoxycarbonylamino-3-(ethoxycarbonylmethyl)-3,4-dihydroquinazolin-6-yl]oxybutyramide;

N-cyclohexyl-N-methyl-4-[2-isopropoxycarbonylamino-3-(ethoxycarbonylmethyl)-3,4-dihydroquinazolin-6-yl]oxybutyramide;

N-cyclohexyl-N-methyl-4-[2-isobutyloxycarbonylamino-3-(ethoxycarbonylmethyl)-3,4-dihydroquinazolin-6-yl]oxybutyramide;

N-cyclohexyl-N-methyl-4-[2-neopentyloxycarbonylamino-3-(ethoxycarbonylmethyl)-3,4-dihydroquinazolin-6-yl]oxybutyramide;

N-cyclohexyl-N-methyl-4-[2-tert-butyloxycarbonylamino-3-(ethoxycarbonylmethyl)-3,4-dihydroquinazolin-6-yl]-oxybutyramide;

N-cyclohexyl-N-methyl-4-[2-phenoxycarbonylamino-3-(ethoxycarbonylmethyl)-3,4-dihydroquinazolin-6-yl]oxybutyramide;

N-cyclohexyl-N-methyl-4-[2-benzyloxycarbonylamino-3-(ethoxycarbonylmethyl)-3,4-dihydroquinazolin-6-yl]oxybutyramide;

N-cyclohexyl-N-methyl-4-[2-(2,6-dimethyl)benzyloxycarbonylamino-3-(ethoxycarbonylmethyl)-3,4-dihydroquinazolin-6-yl]oxybutyramide;

N-cyclohexyl-N-methyl-4-[2-cyclohexyloxycarbonylamino-3-(ethoxycarbonylmethyl)-3,4-dihydroquinazolin-6-yl]oxybutyramide;

N-cyclohexyl-N-methyl-4-[2-ethoxycarbonylamino-3-(tert-butyloxycarbonylmethyl)-3,4-dihyroquinazolin-6-yl]oxybutyramide;

N-cyclohexyl-N-methyl-4-[2-ethoxycarbonylamino-3-(cyclohexyloxy-carbonylmethyl)-3,4-dihydroquinazolin-6-yl]oxybutyramide;

N-cyclohexyl-N-methyl-4-[2-ethoxycarbonylamino-3-(isopropoxycarbonylmethyl)-3,4-dihydroquinazolin-6-yl]oxybutyramide;

N-cyclohexyl-N-methyl-4-[2-ethoxycarbonylamino-3-(2,6-dimethylcyclohexyloxycarbonylmethyl)-3,4-dihydroquinazolin-6-yl]oxybutyramide;

N-cyclohexyl-N-methyl-4-[2-isopropoxycarbonylamino-3-(cyclopentyloxycarbonylmethyl)-3,4-dihydroquinazolin-6-yl]oxybutyramide;

N-cyclohexyl-N-methyl-4-[2-isopropoxycarbonylamino-3-(isobutyloxycarbonylmethyl)-3,4-dihydroquinazolin-6-yl]oxybutyramide;

N-cyclohexyl-N-methyl-4-[2-benzyloxycarbonylamino-3-(neopentyloxycarbonylmethyl)-3,4-dihydroquinazolin-6-yl]oxybutyramide;

N-cyclohexyl-N-methyl-4-[2-benzyloxycarbonylamino-3-(phenoxycarbonylmethyl)-3,4-dihydroquinazolin-6-yl]oxybutyramide;

N-cyclohexyl-N-methyl-4-[2-phenoxycarbonylamino-3-(2,6-dimethylphenoxycarbonylmethyl)-3,4-dihydroquinazolin-6-yl]oxybutyramide;

N-cyclohexyl-N-methyl-4-[2-phenoxycarbonylamino-3-(1-phenylethyloxycarbonylmethyl)-3,4-dihydroquinazolin-6-yl]oxybutyramide;

N-cyclohexyl-N-methyl-4-[2-cyclohexyloxycarbonylamino-3-(2,2-dimethyl-3-butyloxycarbonylmethyl)-3,4-dihydroquinazolin-6-yl]oxybutyramide;

N-cyclohexyl-N-methyl-4-[2-cyclohexyloxycarbonylamino-3-(2-phenyl-2-propyl-oxycarbonylmethyl)-3,4-dihydroquinazolin-6-yl]oxybutyramide;

N-cyclohexyl-N-methyl-4-[2-phenethoxycarbonylamino-3-(benzyloxycarbonylmethyl)-3,4-dihydroquinazolin-6-yl]oxybutyramide;

N-cyclohexyl-N-methyl-4-[2-(4-dimethylamino)phenoxycarbonylamino-3-(2,4,6-trimethylbenzyloxycarbonylmethyl)-3,4-dihydroquinazolin-6-yl]oxybutyramide;

N-cyclohexyl-N-methyl-4-[2-isobutoxycarbonylamino-3-(2-trichloromethyl-2-propyloxycarbonylmethyl)-3,4-dihydroquinazolin-6-yl]oxybutyramide;

N-cyclohexyl-N-methyl-4-[2-cyclohexylmethoxycarbonylamino-3-(2,4,6-trimethylphenyoxycarbonylmethyl)-3,4-dihydroquinazolin-6-yl]oxybutyramide;

N-hexyl-N-methyl-4-[2-ethoxycarbonylamino-3-(tert-butyloxycarbonylmethyl)-3,4-dihydroquinazolin-6-yl]oxybutyramide;

N,N-dimethyl-4-[2-ethoxycarbonylamino-3-(cyclohexyloxycarbonylmethyl)-3,4-dihydroquinazolin-6-yl]oxybutyramide;

N-ethyl-N-methyl-4-[2-ethoxycarbonylamino-3-(isopropyloxycarbonylmethyl)-3,4-dihydroquinazolin-6-yl]oxybutyramide;

N-pentyl-N-methyl-4-[2-ethoxycarbonylamino-3-(2,6-dimethylcyclohexyloxycarbonylmethyl)-3,4-dihydroquinazolin-6-yl]oxybutyramide;

N,N-dihexyl-4-[2-ethoxycarbonylamino-3-(cyclopentyloxycarbonylmethyl)-3,4-dihydroquinazolin-6-yl]oxybutyramide;

N,N-dipentyl-4-[2-benzyloxycarbonylamino-3-(isobutyloxycarbonylmethyl)-3,4-dihydroquinazolin-6-yl]oxybutyramide;

N-cyclohexyl-N-n-hexyl-4-[2-benzyloxycarbonylamino-3-(neopentyloxycarbonylmethyl)-3,4-dihydroquinazolin-6-yl]oxybutyramide;

N-cyclopentyl-N-methyl-4-[2-benzyloxycarbonylamino-3-(2-phenoxycarbonylmethyl)-3,4-dihydroquinazolin6-yl]oxybutyramide;

N-cyclopropylmethyl-N-methyl-4-[2-benzyloxycarbonylamino-3-(2,6-di-methylphenoxycarbonylmethyl)-3,4-dihydroquinazolin-6-yl]oxybutyramide;

N-cycloheptyl-N-methyl-4-[2-benzyloxycarbonylamino-3-(1-phenylethyloxycarbonylmethyl)-3,4-dihydroquinazolin-6-yl]oxybutyramide;

N-cyclopentylbutyl-N-methyl-4-[2-phenoxycarbonylamino-3-(2,2-dimethyl-3-butyloxycarbonylmethyl)-3,4-dihydroquinazolin-6-yl]oxybutyramide;

N-cyclopentylmethyl-N-methyl-4-[2-phenoxycarbonylamino-3-(2-phenyl-2-propyloxycarbonylmethyl)-3,4-dihydroquinazolin-6-yl]oxybutyramide;

N-cyclopentyl-N-butyl-4-[2-phenoxycarbonylamino-3-(benzyloxycarbonylmethyl)-3,4-dihydroquinazolin-6-yl]oxybutyramide;

N,N-dicyclohexyl-4-[2-phenoxycarbonylamino-3-(2,4,6-trimethylbenzyloxycarbonylmethyl)-3,4-dihydroquinazolin-6-yl]-oxybutyramide;

N-phenyl-N-methyl-4-[2-phenoxycarbonylamino-3-(2-trichloromethyl-2-propyloxycarbonylmethyl)-3,4-dihydroquinazolin-6-yl]oxybutyramide;

N-phenyl-N-hexyl-4-[2-phenethyloxycarbonylamino-3-(2,4,6-trimethylphenoxycarbonylmethyl)-3,4-dihydroquinazolin-6-yl]oxybutyramide;

morpholinyl-4-[2-ethoxycarbonylamino-3-(methoxycarbonylmethyl)-3,4-dihydroquinazolin-7-yl]oxybutyramide;

piperidinyl-4-[2-ethoxycarbonylamino-3-(benzyloxycarbonylmethyl)-3,4-dihydroquinazolin-7-yl]oxybutyramide;

pyrrolidinyl-4-[2-ethoxycarbonylamino-3-(tert-butyloxycarbonylmethyl)-3,4-dihydroquinazolin-7-yl]oxybutyramide;

N-methylpiperazinyl-4-[2-ethoxycarbonylamino-3-(neopentyloxycarbonylmethyl)-3,4-dihydroquinazolin-7-yl]oxybutyramide;

tetrahydroquinolinyl-4-[2-ethoxycarbonylamino-3-(isobutyloxycarbonylmethyl)-3,4-dihydroquinazolin-7-yl]oxybutyramide;
tetrahydroisoquinolinyl-4-[2-benzyloxycarbonylamino-3-(2-chlorophenyloxycarbonylmethyl)-3,4-dihydroquinazolin-7-yl]oxybutyramide;
indolinyl-4-[2-benzyloxycarbonylamino-3-(2-dimethylaminophenoxycarbonylmethyl)-3,4-dihydroquinazolin-7-yl]oxybutyramide;
(±)-decahydroquinolinyl-4-[2-benzyloxycarbonylamino-3-(isopropyloxycarbonylmethyl)-3,4-dihydroquinazolin-7-yl]oxybutyramide;
N-cyclohexyl-N-methyl-4-[2-benzyloxycarbonylamino-3-(benzyloxycarbonylmethyl)-3,4-dihydroquinazolin-8-yl]oxybutyramide;
N-cyclohexyl-N-n-hexyl-4-[2-benzyloxycarbonylamino-3-(neopentyloxycarbonylmethyl)-3,4-dihydroquinazolin-8-yl]oxybutyramide;
N-phenyl-N-methyl-4-[2-phenoxycarbonylamino-3-(isobutyloxycarbonylmethyl)-3,4-dihydroquinazolin-8-yl]oxybutyramide;
N-benzyl-N-methyl-4-[2-phenoxycarbonylamino-3-(2-chlorophenoxycarbonylmethyl)-3,4-dihydroquinazolin-8-yl]oxybutyramide;
N,N-dibenzyl-4-[2-phenoxycarbonylamino-3-(2-dimethylaminophenoxycarbonylmethyl)-3,4-dihydroquinazolin-8-yl]oxybutyramide;
N,N-dicyclohexyl-4-[2-phenoxycarbonylamino-3-(isopropyloxycarbonylmethyl)-3,4-dihydroquinazolin-8-yl]oxybutyramide;
(±)-decahydroquinolinyl-4-[2-phenoxycarbonylamino-3-(benzyloxycarbonylmethyl)-3,4-dihydroquinazolin-5-yl]oxybutyramide;
N-phenyl-N-methyl-4-[2-isopropoxycarbonylamino-3-(neopentyloxycarbonylmethyl)-3,4-dihydroquinazolin-5-yl]oxybutyramide;
N-cyclohexyl-N-methyl-4-[2-isopropoxycarbonylamino-3-(isobutyloxycarbonylmethyl)-3,4-dihydroquinazolin-5-yl]oxybutyramide;
N-benzyl-N-methyl-4-[2-isopropoxycarbonylamino-3-(2-chlorophenoxyoxycarbonylmethyl)-3,4-dihydroquinazolin-5-yl]oxybutyramide;
N,N-dibenzyl-4-[2-isopropoxycarbonylamino-3-(2-dimethylaminophenoxyoxycarbonylmethyl)-3,4-dihydroquinazolin-5-yl]oxybutyramide; and
N,N-dicyclohexyl-4-[2-isopropoxycarbonylamino-3-(isopropoxycarbonylmethyl)-3,4-dihydroquinazolin-5-yl]oxybutyramide.

2. Amides

N-cyclohexyl-N-methyl-4-[2-ethoxycarbonylamino-3-carbamoylmethyl-3,4-dihydroquinazolin-6-yl]oxybutyramide;
N-cyclohexyl-N-methyl-4-[2-benzyloxycarbonylamino-3-(N-tert-butylcarbamoylmethyl)-3,4-dihydroquinazolin-6-yl]oxybutyramide;
N-cyclohexyl-N-methyl-4-[2-phenoxycarbonylamino-3-(4-morpholinylcarbonylmethyl)-3,4-dihydroquinazolin-6-yl]oxybutyramide;
N-cyclohexyl-N-methyl-4-[2-cyclohexyloxycarbonylamino-3-(1-piperidinyl-carbonylmethyl)-3,4-dihydroquinazolin-6-yl]oxybutyramide;
N-cyclohexyl-N-methyl-4-[2-phenethoxycarbonylamino-3-N-phenylcarbamoylmethyl)-3,4-dihydroquinazolin-6-yl]oxybutyramide;
N-cyclohexyl-N-methyl-4-[2-(4-dimethylamino)phenoxycarbonylamino-3-N-isopropylcarbamoylmethyl)-3,4-dihydroquinazolin-6-yl]oxybutyramide;
N-cyclohexyl-N-methyl-4-[2-isobutoxycarbonylamino-3-(N,N-dimethylcarbamoylmethyl)-3,4-dihydroquinazolin-6-yl]oxybutyramide;
N-cyclohexyl-N-methyl-4-[2-cyclohexylmethoxycarbonylamino-3-(N-cyclohexylcarbamoylmethyl)-3,4-dihydroquinazolin-6-yl]oxybutyramide;
N-hexyl-N-methyl-4-[2-ethoxycarbonylamino-3-(carbamoylmethyl)-3,4-dihydroquinazolin-6-yl]oxybutyramide;
N,N-dimethyl-4-[2-benzyloxycarbonylamino-3-(N-tert-butylcarbamoylmethyl)-3,4-dihydroquinazolin-6-yl]oxybutyramide;
N-ethyl-N-methyl-4-[2-phenoxycarbonylamino-3-(4-morpholinylcarbamoylmethyl)-3,4-dihydroquinazolin-6-yl]oxybutyramide;
N-pentyl-N-methyl-4-[2-cyclohexylcarbonylamino-3-(1-piperidinylcarbamoylmethyl)-3,4-dihydroquinazolin-6-yl]oxybutyramide;
N,N-dihexyl-4-[2-phenethoxycarbonylamino-3-(N-phenylcarbamoylmethyl)-3,4-dihydroquinazolin-6-yl]oxybutyramide;
N,N-dipentyl-4-[2-(4-dimethylamino)phenoxycarbonylamino-3-N-isopropylcarbamoylmethyl)-3,4-dihydroquinazolin-6-yl]oxybutyramide;
N-cyclohexyl-N-n-hexyl-4-[2-isobutoxycarbonylamino-3-N,N-dimethylcarbamoylmethyl)-3,4-dihydroquinazolin-6-yl]oxybutyramide;
N-cycloheptyl-N-methyl-4-[2-cyclohexylmethoxycarbonylamino-3-(N-cyclohexylcarbamoylmethyl)-3,4-dihydroquinazolin-6-yl]oxybutyramide
morpholinyl-4-[2-ethoxycarbonylamino-3-(N-methylcarbamoylmethyl)-3,4-dihydroquinazolin-7-yl]oxybutyramide;
piperidinyl-4-[2-ethoxycarbonylamino-3-(N-benzylcarbamoylmethyl)-3,4-dihydroquinazolin-7-yl]oxybutyramide;
pyrrolidinyl-4-[2-ethoxycarbonylamino-3-(N-tertbutylcarbamoylmethyl)-3,4-dihydroquinazolin-7-yl]oxybutyramide;
N-methylpiperazinyl-4-[2-ethoxycarbonylamino-3-(N-neopentyl-N-methylcarbamoylmethyl)-3,4-dihydroquinazolin-7-yl]oxybutyramide;
tetrahydroquinolinyl-4-[2-ethoxycarbonylamino-3-(N-propyl-N-iso-butylcarbamoylmethyl)-3,4-dihydroquinazolin-7-yl]oxybutyramide;
tetrahydroisoquinolinyl-4-[2-benzyloxycarbonylamino-3-(N-octyl-N-2-chlorophenylcarbamoylmethyl)-3,4-dihydroquinazolin-7-yl]oxybutyramide;
indolinyl-4-[2-benzyloxycarbonylamino-3-(N-2-dimetylaminophenylcarbamoylmethyl)-3,4-dihydroquinazolin-7-yl]oxybutyramide;
(±)-decahydroquinolinyl-4-[2-benzyloxycarbonylamino-3-(N-cyclohexyl-N-isopropylcarbamoylmethyl)-3,4-dihydroquinazolin-7-yl]oxybutyramide;
N-cyclohexyl-N-methyl-4-[2-benzyloxycarbonylamino-3-(N-benzylcarbamoyl-methyl)-3,4-dihydroquinazolin-8-yl]oxybutyramide;
N-cyclohexyl-N-n-hexyl-4-[2-benzyloxycarbonylamino-3-(N-neopentylcarbamoylmethyl)-3,4-dihydroquinazolin-8-yl]oxybutyramide;
N-phenyl-N-methyl-4-[2-phenoxycarbonylamino-3-(N-isobutylcarbamoylmethyl)-3,4-dihydroquinazolin-8-yl]oxybutyramide;
N-benzyl-N-methyl-4-[2-phenoxycarbonylamino-3-(N-2-chlorophenylcarbamoylmethyl)-3,4-dihydroquinazolin-8-yl]oxybutyramide;

N,N-dibenzyl-4-[2-phenoxycarbonylamino-3-(N-2-dimethylaminophenylcarbamoylmethyl)-3,4-dihydroquinazolin-8-yl]oxybutyramide;

N,N-dicyclohexyl-4-[2-phenoxycarbonylamino-3-(N-isopropylcarbamoylmethyl)-3,4-dihydroquinazolin-8-yl]oxybutyramide;

(±)-decahydroquinolinyl-4-[2-phenoxycarbonylamino-3-(N-benzyoxycarbonylmethyl)-3,4-dihydroquinazolin-5-yl]oxybutyramide;

N-phenyl-N-methyl-4-[2-phenethoxycarbonylamino-3-(N-neopentylcarbamoylmethyl)-3,4-dihydroquinazolin-5-yl]oxybutyramide;

N-cyclohexyl-N-methyl-4-[2-isobutoxycarbonylamino-3-(N,N-di-isobutylcarbamoylmethyl)-3,4-dihydroquinazolin-5-yl]oxybutyramide;

N-benzyl-N-methyl-4-[2-(4-dimethylamino)phenoxycarbonylamino-3-(N-2-chlorophenylcarbamoylmethyl)-3,4-dihydroquinazolin-5-yl]oxybutyramide;

N,N-dibenzyl-4-[2-cyclohexyloxycarbonylamino-3-(N-2-dimethylaminophenylcarbamoylmethyl)-3,4-dihydroquinazolin-5-yl]oxybutyramide; and N,N-dicyclohexyl-4-[2-cyclohexylmethoxycarbonylamino-3-(N-isopropylcarbamoylmethyl)-3,4-dihydroquinazolin-5-yl]oxybutyramide.

EXAMPLE 3

N-Cyclohexyl-N-methyl-4-[2-phenylcarbamoylamino-3-(isopropoxycarbonylmethyl)-3,4-dihydroquinazolin-6-yl]oxybutyramide A. Preparation of the Title Compound by Step F A solution of N-cyclohexyl-N-methyl-4-[2-amino-3-(isopropylcarbonylmethyl)-3,4-dihydroquinazolin-6-yl]oxybutyramide hydrobromide (10.5 g, 20 mmol) and phenylisocyanate (2.4 ml, 22 mmol) dissolved in dichloromethane (50 mL) was treated dropwise with triethylamine. After stirring overnight at room temperature, the reaction was worked up as in Example 1 to afford the title compound as a crystalline solid after chromatography.

B. Preparation of Other Compounds of Formula I (Y=NH) from Compounds of Formula 5 (from Preparation 4)

By substitution of the esters (Z=O) or amides (Z=NH, NR$^3$) of Preparation 4 for the above cited starting material of formula 5, and by optional substitution of other isocyanates for phenyl isocyanate, the following compounds of Formula I may be prepared:

1. Esters

N-cyclohexyl-N-methyl-4-[2-methylcarbamoylamino-3-(ethoxycarbonylmethyl)-3,4-dihydroquinazolin-6-yl]oxybutyramide;

N-cyclohexyl-N-methyl-4-[2-ethylcarbamoylamino-3-(ethoxycarbonylmethyl)-3,4-dihydroquinazolin-6-yl]oxybutyramide;

N-cyclohexyl-N-methyl-4-[2-propylcarbamoylamino-3-(ethoxycarbonylmethyl)-3,4-dihydroquinazolin-6-yl]oxybutyramide;

N-cyclohexyl-N-methyl-4-[2-isopropylcarbamoylamino-3-(ethoxycarbonylmethyl)-3,4-dihydroquinazolin-6-yl]oxybutyramide;

N-cyclohexyl-N-methyl-4-[2-isobutylcarbamoylamino-3-(ethoxycarbonylmethyl)-3,4-dihydroquinazolin-6-yl]oxybutyramide;

N-cyclohexyl-N-methyl-4-[2-tert-butylcarbamoylamino-3-(ethoxycarbonylmethyl)-3,4-dihydroquinazolin-6-yl]oxybutyramide;

N-cyclohexyl-N-methyl-4-[2-phenylcarbamoylamino-3-(ethoxycarbonylmethyl)-3,4-dihydroquinazolin-6-yl]oxybutyramide;

N-cyclohexyl-N-methyl-4-[2-benzylcarbamoylamino-3-(ethoxycarbonylmethyl)-3,4-dihydroquinazolin-6-yl]oxybutyramide;

N-cyclohexyl-N-methyl-4-[2-cyclohexylcarbamoylamino-3-(ethoxycarbonylmethyl)-3,4-dihydroquinazolin-6-yl]oxybutyramide;

N-cyclohexyl-N-methyl-4-[2-(4-methoxy)phenylcarbamoylamino-3-(ethoxycarbonylmethyl)-3,4-dihydroquinazolin-6-yl]oxybutyramide;

N-cyclohexyl-N-methyl-4-[2-(4-dimethylamino)phenylcarbamoylamino-3-(ethoxycarbonylmethyl)-3,4-dihydroquinazolin-6-yl]oxybutyramide;

N-cyclohexyl-N-methyl-4-[2-cyclohexylmethylcarbamoylamino-3-(ethoxycarbonylmethyl)-3,4-dihydroquinazolin-6-yl]oxybutyramide;

N-cyclohexyl-N-methyl-4-[2-ethylcarbamoylamino-3-(tert-butyloxycarbonylmethyl)-3,4-dihydroquinazolin-6-yl]oxybutyramide;

N-cyclohexyl-N-methyl-4-[2-ethylcarbamoylamino-3-(cyclohexyloxy-carbonylmethyl)-3,4-dihydroquinazolin-6-yl]oxubutyramide N-cyclohexyl-N-methyl-4-[2-isopropylcarbamoylamino-3-(isopropoxycarbonylmethyl)-3,4-dihydroquinazolin-6-yl]oxybutyramide;

N-cyclohexyl-N-methyl-4-[2-isopropylcarbamoylamino-3-(2,6-dimethylcyclohexyloxycarbonylmethyl)-3,4-dihydroquinazolin-6-yl]oxybutyramide;

N-cyclohexyl-N-methyl-4-[2-benzylcarbamoylamino-3-(cyclopentyloxycarbonylmethyl)-3,4-dihydroquinazolin-6-yl]oxybutyramide;

N-cyclohexyl-N-methyl-4-[2-benzylcarbamoylamino-3-(isobutyloxycarbonylmethyl)-3,4-dihydroquinazolin-6-yl]oxybutyramide;

N-cyclohexyl-N-methyl-4-[2-cyclohexylcarbamoylamino-3-(neopentyloxycarbonylmethyl)-3,4-dihydroquinazolin-6-yl]oxybutyramide;

N-cyclohexyl-N-methyl-4-[2-cyclohexylcarbamoylamino-3-(phenylcarbonylmethyl)-3,4-dihydroquinazolin-6-yl]oxybutyramide;

N-cyclohexyl-N-methyl-4-[2-phenylcarbamoylamino-3-(2,6-dimethylphenoxycarbonylmethyl)-3,4-dihydroquinazolin-6-yl]oxybutyramide;

N-cyclohexyl-N-methyl-4-[2-phenylcarbamoylamino-3-(1-phenylethyl-oxycarbonylmethyl)-3,4-dihydroquinazolin-6-yl]oxybutyramide;

N-cyclohexyl-N-methyl-4-[2-(4-dimethylamino)phenylcarbamoylamino-3-(2,2-dimethyl-3-butyloxycarbonylmethyl)-3,4-dihydroquinazolin-6-yl]oxybutyramide;

N-cyclohexyl-N-methyl-4-[2-(4-dimethylamino)phenylcarbamoylamino-3-(2-phenyl-2-propyloxycarbonylmethyl)-3,4-dihydroquinazolin-6-yl]oxybutyramide;

N-cyclohexyl-N-methyl-4-[2-tert-butylcarbamoylamino-3-(benzyloxycarbonylmethyl)-3,4-dihydroquinazolin-6-yl]oxybutyramide;

N-cyclohexyl-N-methyl-4-[2-tert-butylcarbamoylamino-3-(2,4,6-trimethylbenzyloxycarbonylmethyl)-3,4-dihydroquinazolin-6-yl]oxybutyramide;

N-cyclohexyl-N-methyl-4-[2-cyclohexylmethylcarbamoylamino-3-(2-trichloromethyl-2-propyloxycarbonylmethyl)-3,4-dihydroquinazolin-6-yl]oxybutyramide;
N-cyclohexyl-N-methyl-4-[2-cyclohexylmethylcarbamoylamino-3-(2,4,6-trimethylphenoxycarbonylmethyl)-3,4-dihydroquinazolin-6-yl]oxybutyramide;
N-hexyl-N-methyl-4-[2-ethylcarbamoylamino-3-(tert-butyloxycarbonylmethyl)-3,4-dihydroquinazolin-6-yl]oxybutyramide;
N,N-dimethyl-4-[2-ethylcarbamoylamino-3-(cyclohexyloxycarbonylmethyl)-3,4-dihydroquinazolin-6-yl]oxybutyramide;
N-ethyl-N-methyl-4-[2-isopropylcarbamoylamino-3-(isopropyloxycarbonylmethyl)-3,4-dihydroquinazolin-6-yl]oxybutyramide;
N-pentyl-N-methyl-4-[2-isopropylcarbamoylamino-3-(2,6-dimethylcyclohexyloxycarbonylmethyl)-3,4-dihydroquinazolin-6-yl]oxybutyramide;
N,N-dihexyl-4-[2-benzylcarbamoylamino-3-(cyclopentyloxycarbonylmethyl)-3,4-dihydroquinazolin-6-yl]oxybutyramide;
N,N-dipentyl-4-[2-benzylcarbamoylamino-3-(isobutyloxycarbonylmethyl)-3,4-dihydroquinazolin-6-yl]oxybutyramide;
N-cyclohexyl-N-n-hexyl-4-[2-phenylcarbamoylamino-3-(neopentyloxycarbonylmethyl)-3,4-dihydroquinazolin-6-yl]oxybutyramide;
N-cyclopentyl-N-methyl-4-[2-phenylcarbamoylamino-3-(2-phenoxycarbonylmethyl)-3,4-dihydroquinazolin6-yl]oxybutyramide;
N-cyclopropylmethyl-N-methyl-4-[2-cyclohexylcarbamoylamino-3-(2,6-di-methylphenoxycarbonylmethyl)-3,4-dihydroquinazolin-6-yl]oxybutyramide;
N-cycloheptyl-N-methyl-4-[2-cyclohexylcarbamoylamino-3-(1-phenethoxycarbonylmethyl)-3,4-dihydroquinazolin-6-yl]oxybutyramide;
N-cyclopentylbutyl-N-methyl-4-[2-(4-dimethylamino)phenylcarbamoylamino-3-(2,2-dimethyl-3-butoxycarbonylmethyl)-3,4-dihydroquinazolin-6-yl]oxybutyramide;
N-cyclopentylmethyl-N-methyl-4-[2-(4-dimethylamino)phenylcarbamoylamino-3-(2-phenyl-2-propyloxycarbonylmethyl)-3,4-dihydroquinazolin-6-yl]oxybutyramide;
N-cyclopentyl-N-butyl-4-[2-tert-butylcarbonylamino-3-(benzyloxycarbonylmethyl)-3,4-dihydroquinazolin-6-yl]oxybutyramide;
N,N-dicyclohexyl-4-[2-tert-butylcarbamoylamino-3-(2,4,6-trimethylbenzyloxycarbonylmethyl)-3,4-dihydroquinazolin-6-yl]oxybutyramide;
N-phenyl-N-methyl-4-[2-cyclohexylmethylcarbamoylamino-3-(2-trichloromethyl-2-propyloxycarbonylmethyl)-3,4-dihydroquinazolin-6-yl]oxybutyramide;
N-phenyl-N-hexyl-4-[2-cyclohexylmethylcarbamoylamino-3-(2,4,6-trimethylphenoxycarbonylmethyl)-3,4-dihydroquinazolin-6-yl]oxybutyramide;
morpholinyl-4-[2-ethylcarbamoylamino-3-(methoxycarbonylmethyl)-3,4-dihydroquinazolin-7-yl]oxybutyramide;
piperidinyl-4-[2-ethylcarbamoylamino-3-(benzyloxycarbonylmethyl)-3,4-dihydroquinazolin-7-yl]oxybutyramide;
pyrrolidinyl-4-[2-ethylcarbamoylamino-3-(tertbutyloxycarbonylmethyl)-3,4-dihydroquinazolin-7-yl]oxybutyramide;
N-methylpiperazinyl-4-[2-ethylcarbamoylamino-3-(neopentyloxycarbonylmethyl)-3,4-dihydroquinazolin-7-yl]oxybutyramide;
tetrahydroquinolinyl-4-[2-ethylcarbamoylamino-3-(isobutyloxycarbonylmethyl)-3,4-dihydroquinazolin-7-yl]oxybutyramide;
tetrahydroisoquinolinyl-4-[2-benzylcarbamoylamino-3-(2-chlorophenoxycarbonylmethyl)-3,4-dihydroquinazolin-7-yl]oxybutyramide;
indolinyl-4-[2-benzylcarbamoylamino-3-(2-dimethylaminophenoxycarbonylmethyl)-3,4-dihydroquinazolin-7-yl]oxybutyramide;
(±)-decahydroquinolinyl-4-[2-benzylcarbamoylamino-3-(isopropyloxycarbonylmethyl)-3,4-dihydroquinazolin-7-yl]oxybutyramide;
N-cyclohexyl-N-methyl-4-[2-benzylcarbamoylamino-3-(benzyloxycarbonylmethyl)-3,4-dihydroquinazolin-8-yl]oxybutyramide;
N-cyclohexyl-N-n-hexyl-4-[2-benzylcarbamoylamino-3-(neopentyloxycarbonylmethyl)-3,4-dihydroquinazolin-8-yl]oxybutyramide;
N-phenyl-N-methyl-4-[2-phenylcarbamoylamino-3-(isobutyloxycarbonylmethyl)-3,4-dihydroquinazolin-8-yl]oxybutyramide;
N-benzyl-N-methyl-4-[2-phenylcarbamoylamino-3-(2-chlorophenoxycarbonylmethyl)-3,4-dihydroquinazolin-8-yl]oxybutyramide;
N,N-dibenzyl-4-[2-phenylcarbamoylamino-3-(2-dimethylaminophenoxycarbonylmethyl)-3,4-dihydroquinazolin-8-yl]oxybutyramide;
N,N-dicyclohexyl-4-[2-phenylcarbamoylamino-3-(isopropyloxycarbonylmethyl)-3,4-dihydroquinazolin-8-yl]oxybutyramide;
(±)-decahydroquinolinyl-4-[2-phenylcarbamoylamino-3-(benzyloxycarbonylmethyl)-3,4-dihydroquinazolin-5-yl]oxybutyramide;
N-phenyl-N-methyl-4-[2-cyclohexylcarbamoylamino-3-(neopentyloxycarbonymethyl)-3,4-dihydroquinazolin-5-yl]oxybutyramide;
N-cyclohexyl-N-methyl-4-[2-(4-dimethylamino)phenylcarbamoylamino-3-(isobutyloxycarbonylmethyl)-3,4-dihydroquinazolin-5-yl]oxybutyramide;
N-benzyl-N-methyl-4-[2-cyclohexylmethylcarbamoylamino-3-(2-chlorophenoxycarbonylmethyl)-3,4-dihydroquinazolin-5-yl]oxybutyramide;
N,N-dibenzyl-4-[2-methylcarbamoylamino-3-(2-dimethylaminophenoxycarbonylmethyl)-3,4-dihydroquinazolin-5-yl]oxybutyramide; and
N,N-dicyclohexyl-4-[2-tert-butylcarbamoylamino-3-(isopropyloxycarbonylmethyl)-3,4-dihydroquinazolin-5-yl]oxybutyramide.

2. Amides

N-cyclohexyl-N-methyl-4-[2-ethylcarbamoylamino-3-(carbamoylmethyl)-3,4-dihydroquinazolin-6-yl]oxybutyramide;
N-cyclohexyl-N-methyl-4-[2-isopropylylcarbamoylamino-3-(N-tert-butylcarbamoylmethyl)-3,4-dihydroquinazolin-6-yl]oxybutyramide;
N-cyclohexyl-N-methyl-4-[2-benzylcarbamoylamino-3-(4morpholinyl-carbonylmethyl)-3,4-dihydroquinazolin-6-yl]oxybutyramide;
N-cyclohexyl-N-methyl-4-[2-cyclohexylcarbamoylamino-3-(1-piperidinyl-carbonylmethyl)-3,4-dihydroquinazolin-6-yl]oxybutyramide;
N-cyclohexyl-N-methyl-4-[2-phenylcarbamoylamino-3-N-phenylcarbamoylmethyl)-3,4-dihydroquinazolin-6-yl]oxybutyramide;
N-cyclohexyl-N-methyl-4-[2-(4-dimethylamino)phenylcarbonylamino-3-N-isopropylcarbamoylmethyl)-3,4-dihydroquinazolin-6-yl]oxybutyramide;

N-cyclohexyl-N-methyl-4-[2-tert-butylcarbonylamino-3-N,N-dimethylcarbamoylmethyl)-3,4-dihydroquinazolin-6-yl]oxybutyramide;

N-cyclohexyl-N-methyl-4-[2-cyclohexylmethylcarbonylamino-3-(N-cyclohexylcarbamoylmethyl)-3,4-dihydroquinazolin-6-yl]oxybutyramide;

N-hexyl-N-methyl-4-[2-ethylcarbamoylamino-3-(carbamoylmethyl)-3,4-dihydroquinazolin-6-yl]oxybutyramide;

N,N-dimethyl-4-[2-benzylcarbamoylamino-3-(N-tert-butylcarbamoylmethyl)-3,4-dihydroquinazolin-6-yl]oxybutyramide;

N-ethyl-N-methyl-4-[2-isopropylcarbamoylamino-3-(4-morpholinyl-carbamoylmethyl)-3,4-dihydroquinazolin-6-yl]oxybutyramide;

N-pentyl-N-methyl-4-[2-cyclohexylcarbamoylamino-3-(1-piperidinylcarbamoylmethyl)-3,4-dihydroquinazolin-6-yl]oxybutyramide;

N,N-dihexyl-4-[2-phenylcarbamoylamino-3-(N-phenylcarbamoylmethyl)-3,4-dihydroquinazolin-6-yl]oxybutyramide;

N,N-dipentyl-4-[2-(4-dimethylamino)phenylcarbamoylamino-3-N-isopropylcarbamoylmethyl)-3,4-dihydroquinazolin-6-yl]oxybutyramide;

N-cyclohexyl-N-n-hexyl-4-[2-tert-butylcarbamoylamino-3-N,N-dimethylcarbamoylmethyl)-3,4-dihydroquinazolin-6-yl]oxybutyramide;

N-cycloheptyl-N-methyl-4-[2-cyclohexylmethylcarbamoylamino-3-((N-cyclohexylcarbamoylmethyl)-3,4-dihydroquinazolin-6-yl]oxybutyramide;

morpholinyl-4-[2-ethylcarbamoylamino-3-(N-methylcarbamoylmethyl)-3,4-dihydroquinazolin-7-yl]oxybutyramide;

piperidinyl-4-[2-ethylcarbamoylamino-3-(N-benzylcarbamoylmethyl)-3,4-dihydroquinazolin-7-yl]oxybutyramide;

pyrrolidinyl-4-[2-ethylcarbamoylamino-3-(N-tert-butylcarbamoylmethyl)-3,4-dihydroquinazolin-7-yl]oxybutyramide;

N-methylpiperazinyl-4-[2-ethylcarbamoylamino-3-(N-neopentyl-N-methylcarbamoylmethyl)-3,4-dihydroquinazolin-7-yl]oxybutyramide;

tetrahydroquinolinyl-4-[2-ethylcarbamoylamino-3-(N-propyl-N-iso-butylcarbamoylmethyl)-3,4-dihydroquinazolin-7-yl]oxybutyramide;

tetrahydroisoquinolinyl-4-[2-benzyl-carbamoylamino-3-(N-octyl-N-2-chlorophenylcarbamoylmethyl)-3,4-dihydroquinazolin-7-yl]oxybutyramide;

indolinyl-4-[2-benzylcarbamoylamino-3-(N-2-dimethylaminophenylcarbamoylmethyl)-3,4-dihydroquinazolin-7-yl]oxybutyramide;

(±)-decahydroquinolinyl-4-[2-benzylcarbamoylamino-3-(N-cyclohexyl-N-isopropylcarbamoylmethyl)-3,4-dihydroquinazolin-7-yl]oxybutyramide;

N-cyclohexyl-N-methyl-4-[2-benzylcarbamoylamino-3-(N-benzylcarbamoyl-methyl)-3,4-dihydroquinazolin-8-yl]oxybutyramide;

N-cyclohexyl-N-n-hexyl-4-[2-benzylcarbamoylamino-3-(N-neopentylcarbamoylmethyl)-3,4-dihydroquinazolin-8-yl]oxybutyramide;

N-phenyl-N-methyl-4-[2-phenylcarbamoylamino-3-(N-isobutylcarbamoylmethyl)-3,4-dihydroquinazolin-8-yl]oxybutyramide;

N-benzyl-N-methyl-4-[2-phenylcarbamoylamino-3-(N-2-chlorophenylcarbamoylmethyl)-3,4-dihydroquinazolin-8-yl]oxybutyramide;

N,N-dibenzyl-4-[2-phenylcarbamoylamino-3-(N-2-dimethyl-aminophenylcarbamoylmethyl)-3,4-dihydroquinazolin-8-yl]oxybutyramide;

N,N-dicyclohexyl-4-[2-phenylcarbamoylamino-3-(N-isopropylcarbamoylmethyl)-3,4-dihydroquinazolin-8-yl]oxybutyramide;

(±)-decahydroquinolinyl-4-[2-phenylcarbamoylamino-3-(N-benzyloxycarbonylmethyl)-3,4-dihydroquinazolin-5-yl]oxybutyramide;

N-phenyl-N-methyl-4-[2-methylcarbamoylamino-3-(N-neopentylcarbamoylmethyl)-3,4-dihydroquinazolin-5-yl]oxybutyramide;

N-cyclohexyl-N-methyl-4-[2-cyclohexylmethylcarbamoylamino-3-(N,N-di-isobutylcarbamoylmethyl)-3,4-dihydroquinazolin-5-yl]oxybutyramide;

N-benzyl-N-methyl-4-[2-(4-dimethylamino)phenylcarbamoylamino-3-(N-2-chlorophenylcarbamoylmethyl)-3,4-dihydroquinazolin-5-yl]oxybutyramide;

N,N-dibenzyl-4-[2-tert-butylcarbamoylamino-3-(N-2-dimethylaminophenylcarbamoylmethyl)-3,4-dihydroquinazolin-5-yl]oxybutyramide; and N,N-dicyclohexyl-4-[2-isopropylcarbamoylamino-3-(N-isopropylcarbamoylmethyl)-3,4-dihydroquinazolin-5-yl]oxybutyramide.

EXAMPLE 4

N-Cyclohexyl-N-methyl-4-[2-N,N-dimethylcarbamoylamino-3-(cyclohexyloxycarbonylmethyl)-3,4-dihydroquinazolin-6-yl]oxybutyramide A. Preparation of the Title Compound by Step G A solution of N-cyclohexyl-N-methyl-4-[2-amino-3-(cyclohexyloxycarbonylmethyl)-3,4-dihydroquinazolin-6-yl]oxybutyramide hydrobromide (5.65 g, 10 mmol) and N,N-dimethylcarbamoyl chloride (1.5 mL) dissolved in dichloromethane (25 mL) was treated dropwise with triethylamine (3.5 mL, 25 mmol). After stirring overnight and the standard workup, the title compound was isolated as an amorphous foam after column chromatography.

B. Preparation of Other Compounds of Formula I (Y=NR) from Compounds of Formula 5 (from Preparation 4)

By substitution of the esters (Z=O) or amides (Z=NH, NR$^3$) of Preparation 4 for the above cited starting material of formula (5), and by optional substitution of other N,N-disubstituted carbamoyl chlorides, the following compounds of Formula I may be prepared:

1. Esters

N-cyclohexyl-N-methyl-4-[2-N,N-dimethylcarbamoylamino-3-(ethoxycarbonylmethyl)-3,4-dihydroquinazolin-6-yl]oxybutyramide;

N-cyclohexyl-N-methyl-4-[2-N,N-diethylcarbamoylamino-3-(ethoxycarbonylmethyl)-3,4-dihydroquinazolin-6-yl]oxybutyramide;

N-cyclohexyl-N-methyl-4-[2-N,N-diphenylcarbamoylamino-3-(ethoxycarbonylmethyl)-3,4-dihydroquinazolin-6-yl]oxybutyramide;

N-cyclohexyl-N-methyl-4-[2-N-methyl-N-cyclohexylcarbamoylamino-3-(ethoxycarbonylmethyl)-3,4-dihydroquinazolin-6-yl]oxybutyramide;

N-cyclohexyl-N-methyl-4-[2-N-methyl-N-phenylcarbamoylamino-3-(ethoxycarbonylmethyl)-3,4-dihydroquinazolin-6-yl]oxybutyramide;

N-cyclohexyl-N-methyl-4-[2-N,N-dibenzylcarbamoylamino-3-(ethoxycarbonylmethyl)-3,4-dihydroquinazolin-6-yl]oxybutyramide;
N-cyclohexyl-N-methyl-4-[2-N-(4-dimethylamino)phenyl-N-methylcarbamoyl-amino-3-(ethoxycarbonylmethyl)-3,4-dihydroquinazolin-6-yl]oxybutyramide;
N-cyclohexyl-N-methyl-4-[2-N-methyl-N-ethylcarbamoylamino-3-(tert-butyloxycarbonylmethyl)-3,4-dihydroquinazolin-6-yl]oxybutyramide;
N-cyclohexyl-N-methyl-4-[2-N-methyl-N-ethylcarbamoylamino-3-(cyclohexyloxycarbonylmethyl)-3,4-dihydroquinazolin-6-yl]oxybutyramide;
N-cyclohexyl-N-methyl-4-[2-N-ethyl-N-phenylcarbamoylamino-3-(isopropoxycarbonylmethyl)-3,4-dihydroquinazolin-6-yl]oxybutyramide;
N-cyclohexyl-N-methyl-4-[2-N-ethyl-N-phenylcarbamoylamino-3-(2,6-dimethylcyclohexyloxycarbonylmethyl)-3,4-dihydroquinazolin-6-yl]oxybutyramide;
N-cyclohexyl-N-methyl-4-[2-N,N-dimethylcarbamoylamino-3-(cyclopentyloxycarbonylmethyl)-3,4-dihydroquinazolin-6-yl]oxybutyramide;
N-cyclohexyl-N-methyl-4-[2-N,N-dimethylcarbamoylamino-3-(isobutyloxycarbonylmethyl)-3,4-dihydroquinazolin-6-yl]oxybutyramide;
N-cyclohexyl-N-methyl-4-[2-N-methyl-N-cyclohexylcarbamoylamino-3-(neopentyloxycarbonylmethyl)-3,4-dihydroquinazolin-6-yl]oxybutyramide;
N-cyclohexyl-N-methyl-4-[2-N-methyl-N-cyclohexylcarbamoylamino-3-(phenoxycarbonylmethyl)-3,4-dihydroquinazolin-6-yl]oxybutyramide;
N-cyclohexyl-N-methyl-4-[2-N,N-diphenylcarbamoylamino-3-(2,6-dimethylphenoxycarbonylmethyl)-3,4-dihydroquinazolin-6-yl]oxybutyramide;
N-cyclohexyl-N-methyl-4-[2-N,N-diphenylcarbamoylamino-3-(1-phenylethyl-oxycarbonylmethyl)-3,4-dihydroquinazolin-6-yl]oxybutyramide;
N-cyclohexyl-N-methyl-4-[2-N,N-dibenzylcarbonylamino-3-(2,2-dimethyl-3-butyloxycarbonylmethyl)-3,4-dihydroquinazolin-6-yl]oxybutyramide;
N-cyclohexyl-N-methyl-4-[2-N,N-dibenzylcarbonylamino-3-(2-phenyl-2-propyl-oxycarbonylmethyl)-3,4-dihydroquinazolin-6-yl]oxybutyramide;
N-cyclohexyl-N-methyl-4-[2-N-(4-dimethylamino)phenyl-N-methylcarbamoylamino-3-(benzyloxycarbonylmethyl)-3,4-dihydroquinazolin-6-yl]oxybutyramide;
N-cyclohexyl-N-methyl-4-[2-N-(4-dimethylamino)phenyl-N-methylcarbamoylamino-3-(2,4,6-trimethylbenzyloxycarbonylmethyl)-3,4-dihydroquinazolin-6-yl]oxybutyramide;
N-cyclohexyl-N-methyl-4-[2-N,N-dicyclohexylcarbamoylamino-3-(2-trichloromethyl-2-propyloxycarbonylmethyl)-3,4-dihydroquinazolin-6-yl]oxybutyramide;
N-cyclohexyl-N-methyl-4-[2-N,N-dicyclohexylcarbamoylamino-3-(2,4,6-trimethylphenyoxycarbonylmethyl)-3,4-dihydroquinazolin-6-yl]oxybutyramide;
N-hexyl-N-methyl-4-[2-N-methyl-N-ethylcarbamoylamino-3-(tert-butyloxycarbonylmethyl)-3,4-dihydroquinazolin-6-yl]oxybutyramide;
N,N-dimethyl-4-[2-N-methyl-N-ethylcarbamoylamino-3-(cyclohexyloxycarbonylmethyl)-3,4-dihydroquinazolin-6-yl]oxybutyramide;
N-ethyl-N-methyl-4-[2-N-ethyl-N-phenylcarbamoylamino-3-(isopropyloxycarbonylmethyl)-3,4-dihydroquinazolin-6-yl]oxybutyramide;
N-pentyl-N-methyl-4-[2-N-ethyl-N-phenylcarbamoylamino-3-(2,6-dimethylcyclohexyloxycarbonylmethyl)-3,4-dihydroquinazolin-6-yl]oxybutyramide;
N,N-dihexyl-4-[2-N,N-dimethylcarbamoylamino-3-(cyclopentyloxycarbonylmethyl)-3,4-dihydroquinazolin-6-yl]oxybutyramide;
N,N-dipentyl-4-[2-N,N-dimethylcarbamoylamino-3-(isobutyloxycarbonylmethyl)-3,4-dihydroquinazolin-6-yl]oxybutyramide;
N-cyclohexyl-N-n-hexyl-4-[2-N-methyl-N-cyclohexylcarbamoylamino-3-(neopentyloxycarbonylmethyl)-3,4-dihydroquinazolin-6-yl]oxybutyramide;
N-cyclopentyl-N-methyl-4-[2-N-methyl-N-cyclohexylcarbamoylamino-3-(2-phenoxycarbonylmethyl)-3,4-dihydroquinazolin6-yl]oxybutyramide;
N-cyclopropylmethyl-N-methyl-4-[2-N,N-diphenylcarbamoylamino-3-(2,6-dimethylphenoxycarbonylmethyl)-3,4-dihydroquinazolin-6-yl]oxybutyramide;
N-cycloheptyl-N-methyl-4-[2-N,N-diphenylcarbamoylamino-3-(1-phenethoxycarbonylmethyl)-3,4-dihydroquinazolin-6-yl]oxybutyramide;
N-cyclopentylbutyl-N-methyl-4-[2-N,N-dibenzylcarbamoylamino-3-(2,2-dimethyl-3-butyloxycarbonylmethyl)-3,4-dihydroquinazolin-6-yl]oxybutyramide;
N-cyclopentylmethyl-N-methyl-4-[2-N,N-dibenzylcarbamoylamino-3-(2-phenyl-2-propyloxycarbonylmethyl)-3,4-dihydroquinazolin-6-yl]oxybutyramide;
N-cyclopentyl-N-butyl-4-[2-N-(4-dimethylamino)phenyl-N-methylcarbamoylamino-3-(benzyloxycarbonylmethyl)-3,4-dihydroquinazolin-6-yl]oxybutyramide;
N,N-dicyclohexyl-4-[2-N-(4-dimethylamino)phenyl-N-methylcarbamoylamino-3-(2,4,6-trimethylbenzyloxycarbonylmethyl)-3,4-dihydroquinazolin-6-yl]oxybutyramide;
N-phenyl-N-methyl-4-[2-N,N-dicyclohexylcarbamoylamino-3-(2-trichloromethyl-2-propyloxycarbonylmethyl)-3,4-dihydroquinazolin-6-yl]oxybutyramide;
N-phenyl-N-hexyl-4-[2-N,N-dicyclohexylcarbamoylamino-3-(2,4,6-trimethylphenoxycarbonylmethyl)-3,4-dihydroquinazolin-6-yl]oxybutyramide;
morpholinyl-4-[2-N,N-dimethylcarbamoylamino-3-(methoxycarbonylmethyl)-3,4-dihydroquinazolin-7-yl]oxybutyramide;
piperidinyl-4-[2-N,N-dimethylcarbamoylamino-3-(benzyloxycarbonylmethyl)-3,4-dihydroquinazolin-7-yl]oxybutyramide;
pyrrolidinyl-4-[2-N,N-dimethylcarbamoylamino-3-(tert-butyloxycarbonylmethyl)-3,4-dihydroquinazolin-7-yl]oxybutyramide;
N-methylpiperazinyl-4-[2-N,N-dimethylcarbamoylamino-3-(neopentyloxycarbonylmethyl)-3,4-dihydroquinazolin-7-yl]oxybutyramide;
tetrahydroquinolinyl-4-[2-N,N-dimethylcarbamoylamino-3-(isobutyloxycarbonylmethyl)-3,4-dihydroquinazolin-7-yl]oxybutyramide;
tetrahydroisoquinolinyl-4-[2-N-methyl-N-cyclohexylcarbamoylamino-3-(2-chlorophenoxycarbonylmethyl)-3,4-dihydroquinazolin-7-yl]oxybutyramide;
indolinyl-4-[2-N-methyl-N-cyclohexylcarbamoylamino-3-(2-dimethylaminophenoxycarbonylmethyl)-3,4-dihydroquinazolin-7-yl]oxybutyramide;
(±)-decahydroquinolinyl-4-[2-N-methyl-N-cyclohexylcarbamoylamino-3-(isopropyloxycarbonylmethyl)-3,4-dihydroquinazolin-7-yl]oxybutyramide;

N-cyclohexyl-N-methyl-4-[2-N-methyl-N-cyclohexylcarbamoylamino-3-(benzyloxycarbonylmethyl)-3,4-dihydroquinazolin-8-yl]oxybutyramide;

N-cyclohexyl-N-n-hexyl-4-[2-N-methyl-N-cyclohexylcarbamoylamino-3-(neopentyloxycarbonylmethyl)-3,4-dihydroquinazolin-8-yl]oxybutyramide;

N-phenyl-N-methyl-4-[2-N,N-dibenzylcarbamoylamino-3-(isobutyloxycarbonylmethyl)-3,4-dihydroquinazolin-8-yl]oxybutyramide;

N-benzyl-N-methyl-4-[2-N,N-dibenzylcarbamoylamino-3-(2-chlorophenoxycarbonylmethyl)-3,4-dihydroquinazolin-8-yl]oxybutyramide;

N,N-dibenzyl-4-[2-N,N-dibenzylcarbamoylamino-3-(2-dimethylaminophenoxycarbonylmethyl)-3,4-dihydroquinazolin-8-yl]oxybutyramide;

N,N-dicyclohexyl-4-[2-N,N-dibenzylcarbamoylamino-3-(isopropyloxycarbonylmethyl)-3,4-dihydroquinazolin-8-yl]oxybutyramide;

(±)-decahydroquinolinyl-4-[2-N,N-dibenzylcarbamoylamino-3-(benzyloxycarbonylmethyl)-3,4-dihydroquinazolin-5-yl]oxybutyramide;

N-phenyl-N-methyl-4-[2-N,N-diphenylcarbamoylamino-3-(neopentyloxycarbonylmethyl)-3,4-dihydroquinazolin-5-yl]oxybutyramide;

N-cyclohexyl-N-methyl-4-[2-N-ethyl-N-phenylcarbamoylamino-3-(isobutyloxycarbonylmethyl)-3,4-dihydroquinazolin-5-yl]oxybutyramide;

N-benzyl-N-methyl-4-[2-N-(4-dimethylamino)phenyl-N-methylcarbamoylamino-3-(2-chlorophenoxycarbonylmethyl)-3,4-dihydroquinazolin-5-yl]oxybutyramide;

N,N-dibenzyl-4-[2-N,N-dicyclohexylcarbamoylamino-3-(2-dimethylaminophenoxycarbonylmethyl)-3,4-dihydroquinazolin-5-yl]oxybutyramide; and N,N-dicyclohexyl-4-[2-N-methyl-N-ethylcarbamoylamino-3-(isopropyloxycarbonylmethyl)-3,4-dihydroquinazolin-5-yl]oxybutyramide.

2. Amides

N-cyclohexyl-N-methyl-4-[2-N,N-dimethylcarbamoylamino-3-(carbamoylmethyl)-3,4-dihydroquinazolin-6-yl]oxybutyramide;

N-cyclohexyl-N-methyl-4-[2-N-methyl-N-cyclohexylcarbamoylamino-3-(N-tert-butylcarbamoylmethyl)-3,4-dihydroquinazolin-6-yl]oxybutyramide;

N-cyclohexyl-N-methyl-4-[2-N-methyl-N-ethylcarbamoylamino-3-(4-morpholinyl-carbonylmethyl)-3,4-dihydroquinazolin-6-yl]oxybutyramide;

N-cyclohexyl-N-methyl-4-[2-N-ethyl-N-phenylcarbamoylamino-3-(1-piperidinyl-carbonylmethyl)-3,4-dihydroquinazolin-6-yl]oxybutyramide;

N-cyclohexyl-N-methyl-4-[2-N,N-diphenylcarbamoylamino-3-N-phenylcarbamoylmethyl)-3,4-dihydroquinazolin-6-yl]oxybutyramide;

N-cyclohexyl-N-methyl-4-[2-N,N-dibenzylcarbamoylamino-3-N-isopropylcarbamoylmethyl)-3,4-dihydroquinazolin-6-yl]oxybutyramide;

N-cyclohexyl-N-methyl-4-[2-N-(4-dimethylamino)phenyl-N-methylcarbamoylamino-3-N,N-dimethylcarbamoylmethyl)-3,4-dihydroquinazolin-6-yl]oxybutyramide;

N-cyclohexyl-N-methyl-4-[2-N,N-dicyclohexylcarbamoylamino-3-(N-cyclohexylcarbamoylmethyl)-3,4-dihydroquinazolin-6-yl]oxybutyramide;

N-hexyl-N-methyl-4-[2-N,N-dimethylcarbamoylamino-3-(carbamoylmethyl)-3,4-dihydroquinazolin-6-yl]oxybutyramide;

N,N-dimethyl-4-[2-N-methyl-N-cyclohexylcarbamoylamino-3-(N-tert-butylcarbamoylmethyl)-3,4-dihydroquinazolin-6-yl]oxybutyramide;

N-ethyl-N-methyl-4-[2-N-methyl-N-ethylcarbamoylamino-3-(4-morpholinylcarbamoylmethyl)-3,4-dihydroquinazolin-6-yl]oxybutyramide;

N-pentyl-N-methyl-4-[2-N-ethyl-N-phenylcarbamoylamino-3-(1-piperidinylcarbamoylmethyl)-3,4-dihydroquinazolin-6-yl]oxybutyramide;

N,N-dihexyl-4-[2-N,N-diphenylcarbamoylamino-3-(N-phenylcarbamoylmethyl)-3,4-dihydroquinazolin-6-yl]oxybutyramide;

N,N-dipentyl-4-[2-N,N-dibenzylcarbamoylamino-3-N-isopropylcarbamoylmethyl)-3,4-dihydroquinazolin-6-yl]oxybutyramide;

N-cyclohexyl-N-n-hexyl-4-[2-N-(4-dimethylamino)phenyl-N-methylcarbamoylamino-3-N,N-dimethylcarbamoylmethyl)-3,4-dihydroquinazolin-6-yl]oxybutyramide;

N-cycloheptyl-N-methyl-4-[2-N,N-dicyclohexylcarbamoylamino-3-((N-cyclohexylcarbamoylmethyl)-3,4-dihydroquinazolin-6-yl]oxybutyramide;

morpholinyl-4-[2-N,N-dimethylcarbamoylamino-3-(N-methylcarbamoylmethyl)-3,4-dihydroquinazolin-7-yl]oxybutyramide;

piperidinyl-4-[2-N,N-dimethylcarbamoylamino-3-(N-benzylcarbamoylmethyl)-3,4-dihydroquinazolin-7-yl]oxybutyramide;

pyrrolidinyl-4-[2-N,N-dimethylcarbamoylamino-3-(N-tert-butylcarbamoylmethyl)-3,4-dihydroquinazolin-7-yl]oxybutyramide;

N-methylpiperazinyl-4-[2-N,N-dimethylcarbamoylamino-3-(N-neopentyln-methyl-carbamoylmethyl)-3,4-dihydroquinazolin-7-yl]oxybutyramide;

tetrahydroquinolinyl-4-[2-N,N-dimethylcarbamoylamino-3-(N-propyl-N-iso-butylcarbamoylmethyl)-3,4-dihydroquinazolin-7-yl]oxybutyramide;

tetrahydroisoquinolinyl-4-[2-N-methyl-N-cyclohexylcarbamoylamino-3-(N-octyl-N-2-chlorophenylcarbamoylmethyl)-3,4-dihydroquinazolin-7-yl]oxybutyramide;

indolinyl-4-[2-N-methyl-N-cyclohexylcarbamoylamino-3-(N-2-dimethylaminophenylcarbamoylmethyl)-3,4-dihydroquinazolin-7-yl]oxybutyramide;

(±)-decahydroquinolinyl-4-[2-N-methyl-N-cyclohexylcarbamoylamino-3-(N-cyclohexyl-N-isopropylcarbamoylmethyl)-3,4-dihydroquinazolin-7-yl]oxybutyramide;

N-cyclohexyl-N-methyl-4-[2-N-methyl-N-cyclohexylcarbamoylamino-3-(N-benzylcarbamoyl-methyl)-3,4-dihydroquinazolin-8-yl]oxybutyramide;

N-cyclohexyl-N-n-hexyl-4-[2-N-methyl-N-cyclohexylcarbamoylamino-3-(N-neopentylcarbamoylmethyl)-3,4-dihydroquinazolin-8-yl]oxybutyramide;

N-phenyl-N-methyl-4-[2-N,N-diphenylcarbamoylamino-3-(N-isobutylcarbamoylmethyl)-3,4-dihydroquinazolin-8-yl]oxybutyramide;

N-benzyl-N-methyl-4-[2-N,N-diphenylcarbamoylamino-3-(N-2-chlorophenylcarbamoylmethyl)-3,4-dihydroquinazolin-8-yl]oxybutyramide;

N,N-dibenzyl-4-[2-N,N-diphenylcarbamoylamino-3-(N-2-dimethylaminophenylcarbamoylmethyl)-3,4-dihydroquinazolin-8-yl]oxybutyramide;

N,N-dicyclohexyl-4-[2-N,N-diphenylcarbamoylamino-3-(N-isopropylcarbamoylmethyl)-3,4-dihydroquinazolin-8-yl]oxybutyramide;

(±)-decahydroquinolinyl-4-[2-N,N-diphenylcarbamoylamino-3-(N-benzyloxycarbonylmethyl)-3,4-dihydroquinazolin-5-yl]oxybutyramide;
N-phenyl-N-methyl-4-[2-N,N-dibenzylcarbamoylamino-3-(N-neopentylcarbamoylmethyl)-3,4-dihydroquinazolin-5-yl]oxybutyramide;
N-cyclohexyl-N-methyl-4-[2-N-methyl-N-ethylcarbamoylamino-3-(N,N-di-isobutylcarbamoylmethyl)-3,4-dihydroquinazolin-5-yl]oxybutyramide;
N-benzyl-N-methyl-4-[2-N,N-dicyclohexylcarbamoylamino-3-(N-2-chlorophenylcarbamoylmethyl)-3,4-dihydroquinazolin-5-yl]oxybutyramide;
N,N-dibenzyl-4-[2-N-phenyl-N-ethylcarbamoylamino-3-(N-2-dimethylaminophenylcarbamoylmethyl)-3,4-dihydroquinazolin-5-yl]oxybutyramide; and
N,N-dicyclohexyl-4-[2-N,N-dicyclohexylcarbamoylamino-3-(N-isopropylcarbamoylmethyl)-3,4-dihydroquinazolin-5-yl]oxybutyramide.

EXAMPLE 5

N-Cyclohexyl-N-Methyl-4-[2-acetamido-3-ethoxycarbonylmethyl-3,4-dihydroquinazolin-6-yl]oxybutyramide A solution of N-cyclohexyl-N-methyl-4-[2-acetamido-3-tert-butyloxycarbonylmethyl-3,4-dihydroquinazolin-6-yl]oxybutyramide (13.7 g, 25 mmol) was dissolved in a mixture of ethyl acetate and ethanol (10 mL each), and to the mixture was added saturated HBr in acetic acid. After stirring overnight, the mixture was concentrated, dissolved in ethyl acetate and the organic layer was washed with half-saturated sodium bicarbonate and brine, otherwise dried, filtered and evaporated. Column chromatography over silica gel (3:1 dichloromethane-ethyl acetate) afforded the title compound as an amorphous foam which crystalled from cold ether, mp 96°–7° C.

Treatment of any tert-butyl ester ($ZR^1$=O-tert-butyl) of Formula 1, excluding N-Boc derivatives ($YR^2$=O-tert-butyl), with acid and the appropriate alcohol $R^1OH$, the corresponding ester ($ZR^1$=$OR^1$) can be prepared.

EXAMPLE 6

N-Cyclohexyl-N-methyl-4-[2-acetamido-3-carboxymethyl-3,4-dihydroquinazolin-6-yl]oxybutyramide hydrochloride (Z=O, $R^1$=H)

A solution of N-cyclohexyl-N-methyl-4-[2-acetamido-3-tert-butoxycarbonylmethyl-3,4-dihydroquinazolin-6-yl]oxybutyramide in ethyl acetate saturated with hydrogen chloride was stirred for 1 hour at room temperature. The resulting precipitate was collected by filtration and dried to afford the title compound as a hygroscopic solid.

Using the appropriate tert-butyl ester ($ZR^1$=O-tert-butyl) and excluding Boc-protected derivatives ($YR^2$=O-tert-butyl), treatment with acid will afford the corresponding 3-carboxymethyl derivative ($ZR^1$=OH).

EXAMPLE 7

Conversion of Free Base to Salt

A solution of N-cyclohexyl-N-methyl-4-[2-acetamido-3-ethoxycarbonylmethyl-3,4-dihydroquinazolin-6-yl]oxybutyramide in ethyl acetate was treated dropwise with hydrogen chloride in ethyl acetate. Addition of ether and filtration of the resulting precipitate afforded the corresponding hydrochloride salt as a hygroscopic powder, m.p. 67°–69° C.

Under similar conditions, any compound of Formula I, prepared in Examples 1–4, excepting those where $YR^2$ or $ZR^1$ is O-tert-butyl, can be converted to its corresponding acid addition salt by use of the appropriate inorganic or organic acid. Where either $YR^2$ or $ZR^1$ is O-tert-butyl, only acids with a $pK_a$ greater than about 2 to 3 can be used in order to avoid cleavage of these groups.

EXAMPLE 8

Compounds of the present invention, either the free base or a pharmaceutically acceptable acid addition salt, may be orally administered to a subject as a tablet. While the active ingredient may comprise anywhere between 1 and 99 percent of the formulation that percentage preferably will be an amount which will cause to be delivered to the subject, the active ingredient in an amount of between 20 mg and 100 mg per tablet. Following is a representative tablet formulation in which the active ingredient is N-cyclohexyl-N-methyl-4-[2-acetamido-3-ethoxycarbonylmethyl)-3,4-dihydroquinazolin-6-yl)oxybutyramide hydrobromide. However, the formulation profile given below may be used to formulate a tablet for any of the compounds represented by Formula I.

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 9

An alternative oral dosage form is to fill hard shell gelatin capsules with a powder containing the active ingredient in the desired amount. Using the active ingredient mentioned in Example 6 above, the acid addition salts, or any other compound according to Formula I there may be prepared an exemplary hard shell gelatin capsule formulation using the following ingredients:

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 10

Alternatively, compounds of the present invention may be prepared as a suspension of oral administration. Any of the compounds of Formula I, either in free base form or as the acid addition salt, may be used in this formulation.

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 11

Inotropic Activity of the Compounds of the Present Invention

Mongrel dogs were anesthetized intravenously with 35 mg/Kg sodium pentobarbital and supplemented as needed. Blood pressure was measured with a Statham pressure transducer via a cannula inserted from a femoral artery into the abdominal aorta. Heart rate was recorded by a cardiotachometer from a lead II electrocardiogram. Right ventricular contractile force was recorded from a Walton-Brodie strain gauge sutured to the right ventricle following a midsternal thoracotomy. A Harvard respirator was used to ventilate the dogs with room air through an endotracheal tube. The dog was bilaterally vagotomized. Following a midline laparotomy, a cannula was sutured into the duodenum for intraduodenal administration of test compound. A femoral vein was cannulated for administration of isoproterenol. All data were recorded on a Beckman R611 Dynograph.

To assess the responsiveness of each dog, isoproterenol was given intravenously at half-dog interval doses from 0.007 to 2.1 or 6.67 mcg/Kg. The test compound was then administered intraduodenally, at dose levels from 0.01 to 3.2 mg/Kg.

The test results are summarized in the following Table

TABLE I

| Compound | dose (mg/kg, i.d.) | Peak Effects as % of Max. Isoproterenol | | |
|---|---|---|---|---|
| | | Rt. Ventricular Contractile Force | Heart Rate | Blood Pressure |
| N—cyclohexyl-N—methyl-4-[2-acetamido-3-(ethoxycarbonyl-methyl)-3,4-dihydro-quinazolin-6-yl]oxybutyramide | 0.01 | 3 | 3 | 4 |
| | 0.03 | 5 | 5 | 4 |
| | 0.1 | 6 | 6 | 14 |
| | 0.3 | 22 | 19 | 9 |
| | 1.0 | 54 | 34 | 35 |
| | 3.2 | 58 | 40 | 50 |

What is claimed is:

1. A compound of the formula

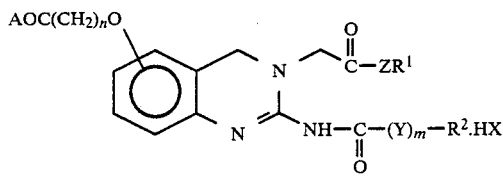

or an optical isomer thereof wherein
Y is O or NR$^4$;
Z is O or NR$^3$;
m is 0 or 1;
n is an integer of 1 to 6;
R$^1$, R$^2$, R$^3$ and R$^4$ are independently hydrogen, except that when m is 1 and Y is O, R$^2$ is not hydrogen; alkyl of 1 to 12 carbon atoms optionally substituted with a trichloromethyl or trifluoromethyl radical; cycloalkyl of 3 to 12 carbon atoms optionally substituted with up to two lower alkyl radicals; cycloalkyl lower alkyl of 4 to 12 carbon atoms optionally substituted on the cycloalkyl ring with up to two lower alkyl radicals; and phenyl or phenyl lower alkyl wherein the phenyl ring is optionally substituted with at least one lower alkyl, halo or lower alkoxy group or an —N(R$^5$)$_2$ group wherein R$^5$ is lower alkyl;
or independently when Y is NR$^4$ or when Z is NR$^3$, R$^2$ and R$^4$ can optionally form a first pair and R$^1$ and R$^3$ can optionally independently form a second pair respectively, in which the respective pair is combined with the N to which it is attached to form a radical selected from the group consisting of morpholinyl, piperidinyl, N-loweralkylpiperazinyl, N-arylpiperazinyl, and pyrrolidinyl;
HX is optionally present and when present represents the acid portion of a pharmaceutically acceptable acid addition salt;
A is NR$^6$R$^7$ wherein R$^6$ and R$^7$ are independently selected from the group consisting of: hydrogen; alkyl of 1 to 6 carbon atoms; cycloalkyl of 3 to 8 carbon atoms or cycloalkyl lower alkyl of 4 to 12 carbon atoms wherein the cycloalkyl ring is optionally substituted with a lower alkyl, lower alkoxy, —OCOR$^5$, halo, —N(R$^5$)$_2$, —NHCOR$^5$, or —COOR$^5$ group wherein R$^5$ is lower alkyl; and phenyl or phenyl lower alkyl wherein phenyl is optionally substituted with at least one lower alkyl, halo or lower alkoxy group or an —N(R$^5$)$_2$, —NHCOR$^5$, or —COOR$^5$ group wherein R$^5$ is lower alkyl; or wherein R$^6$ and R$^7$ are combined with the nitrogen to which it is attached to form a radical selected from the group consisting of: morpholinyl, piperidinyl, perhexylenyl, N-loweralkylpiperazinyl, pyrrolidinyl, tetrahydroquinolinyl, tetrahydroisoquinolinyl, (±)-decahydroquinolinyl and indolinyl.

2. A compound of claim 1 wherein n is 3 or 4.

3. A compound of claim 2 wherein AOC(CH$_2$)$_n$O is attached at position 6 of the quinazoline ring.

4. A compound of claim 3 wherein R$^6$ is alkyl of 1 to 6 carbon atoms and R$^7$ is cycloalkyl of 3 to 8 carbon atoms.

5. A compound of claim 4 wherein R$^6$ is methyl and R$^7$ is cyclohexyl.

6. A compound of claim 5 wherein n is 3.

7. A compound of claim 6 wherein R$^1$ is hydrogen, alkyl, cycloalkyl, cycloalkyl lower alkyl, optionally lower alkyl substituted phenyl, or phenyl lower alkyl optionally substituted with lower alkyl on the phenyl ring.

8. A compound of claim 6 wherein R$^1$ is an alkyl radical having more than three carbon atoms and branching at the first or second carbon atom from the oxygen atom.

9. A compound of claim 6 wherein Z is O.

10. A compound of claim 9 wherein m is 0.

11. A compound of claim 10 wherein R$^1$ is ethyl.

12. A compound of claim 11 wherein $R^2$ is a lower alkyl or phenyl radical.

13. The compound of claim 11 which is N-cyclohexyl-N-methyl-4-[2-acetamido-3-(ethoxycarbonylmethyl-methyl)-3,4-dihydroquinozolin-6-yl]-oxybutyramide or a pharmaceutically acceptable salt thereof.

14. A compound of the formula

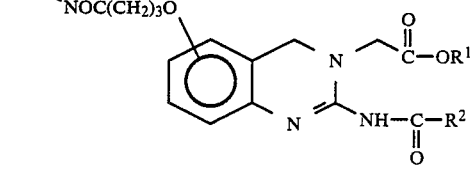

or an optical isomer thereof wherein:

$R^1$ is alkyl of 1 to 12 carbon atoms, cycloalkyl of 3 to 12 carbon atoms, or cycloalkyl lower alkyl of 4 to 12 carbon atoms; and $R^2$ is a lower alkyl or aryl radical.

15. A compound of claim 14 in which $R^1$ and $R^2$ are lower alkyl.

16. A compound of claim 14 in which $R^1$ has more than three carbon atoms and branches at the first or second carbon atom from the oxygen atom.

17. A compound of claim 15 in which $R^1$ is ethyl.

18. A compound of claim 17 wherein $R^2$ is lower alkyl or phenyl.

* * * * *